(12) United States Patent
Sauer

(10) Patent No.: US 12,207,821 B2
(45) Date of Patent: Jan. 28, 2025

(54) DEVICE FOR CARDIAC SURGERY

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 379 days.

(21) Appl. No.: 17/847,445

(22) Filed: Jun. 23, 2022

(65) Prior Publication Data

US 2023/0009669 A1  Jan. 12, 2023

Related U.S. Application Data

(60) Provisional application No. 63/219,011, filed on Jul. 7, 2021, provisional application No. 63/219,017, filed on Jul. 7, 2021.

(51) Int. Cl.
*A61B 17/11* (2006.01)

(52) U.S. Cl.
CPC ....... *A61B 17/11* (2013.01); *A61B 2017/1107* (2013.01)

(58) Field of Classification Search
CPC ... A61B 17/0491; A61B 17/11; A61B 17/115; A61B 2017/06061; A61B 2017/1103; A61B 2017/1107; A61B 2017/1125; A61B 2017/1132; A61B 2017/1135; A61B 2017/291; A61B 2017/292; A61B 2017/294

See application file for complete search history.

(56) References Cited

U.S. PATENT DOCUMENTS

| | | | |
|---|---|---|---|
| 5,320,628 A * | 6/1994 | Ufkin | A61B 90/11 604/116 |
| 6,013,027 A * | 1/2000 | Khan | A61B 17/02 600/201 |
| 6,050,266 A | 4/2000 | Benetti et al. | |
| 6,613,058 B1 | 9/2003 | Goldin | |
| 6,869,437 B1 | 3/2005 | Hausen et al. | |

(Continued)

FOREIGN PATENT DOCUMENTS

| | | |
|---|---|---|
| EP | 938870 | 9/1999 |
| WO | 96/25886 | 8/1996 |
| WO | 2020/186189 | 9/2020 |

OTHER PUBLICATIONS

Extended EP Search Report for Application No. 22183381.7; dated Nov. 25, 2022, 9 pages.

*Primary Examiner* — Elizabeth Houston
*Assistant Examiner* — Lindsey Bachman
(74) *Attorney, Agent, or Firm* — Michael E. Coyne

(57) ABSTRACT

A medical device assembly includes a hinge rod having a first portion and a second portion, and a pedestal is coupled to the second portion of the hinge rod, the pedestal having a top surface, and portions of the pedestal cooperate to define a trough that is configured to hold a first portion of a vessel on the top surface of the pedestal. A retainer is movably coupled to the pedestal, and the retainer has a planar member having a lower surface configured to oppose the top surface of the pedestal. A joint member is coupled to the hinge rod, and a clamp assembly is releasably coupled to the joint member such that when the clamp assembly is in a locked configuration, the hinge rod is not repositionable, and when the clamp assembly is in an unlocked configuration, the hinge rod is repositionable.

18 Claims, 22 Drawing Sheets

(56) References Cited

U.S. PATENT DOCUMENTS

| | | | |
|---|---|---|---|
| 8,721,630 B2* | 5/2014 | Ortiz | A61B 34/70 |
| | | | 606/1 |
| 2001/0029384 A1 | 10/2001 | Nicholas et al. | |
| 2010/0219227 A1* | 9/2010 | Whitman | A61B 17/07207 |
| | | | 227/175.1 |
| 2020/0011461 A1* | 1/2020 | Mellinger | F16L 23/06 |

* cited by examiner

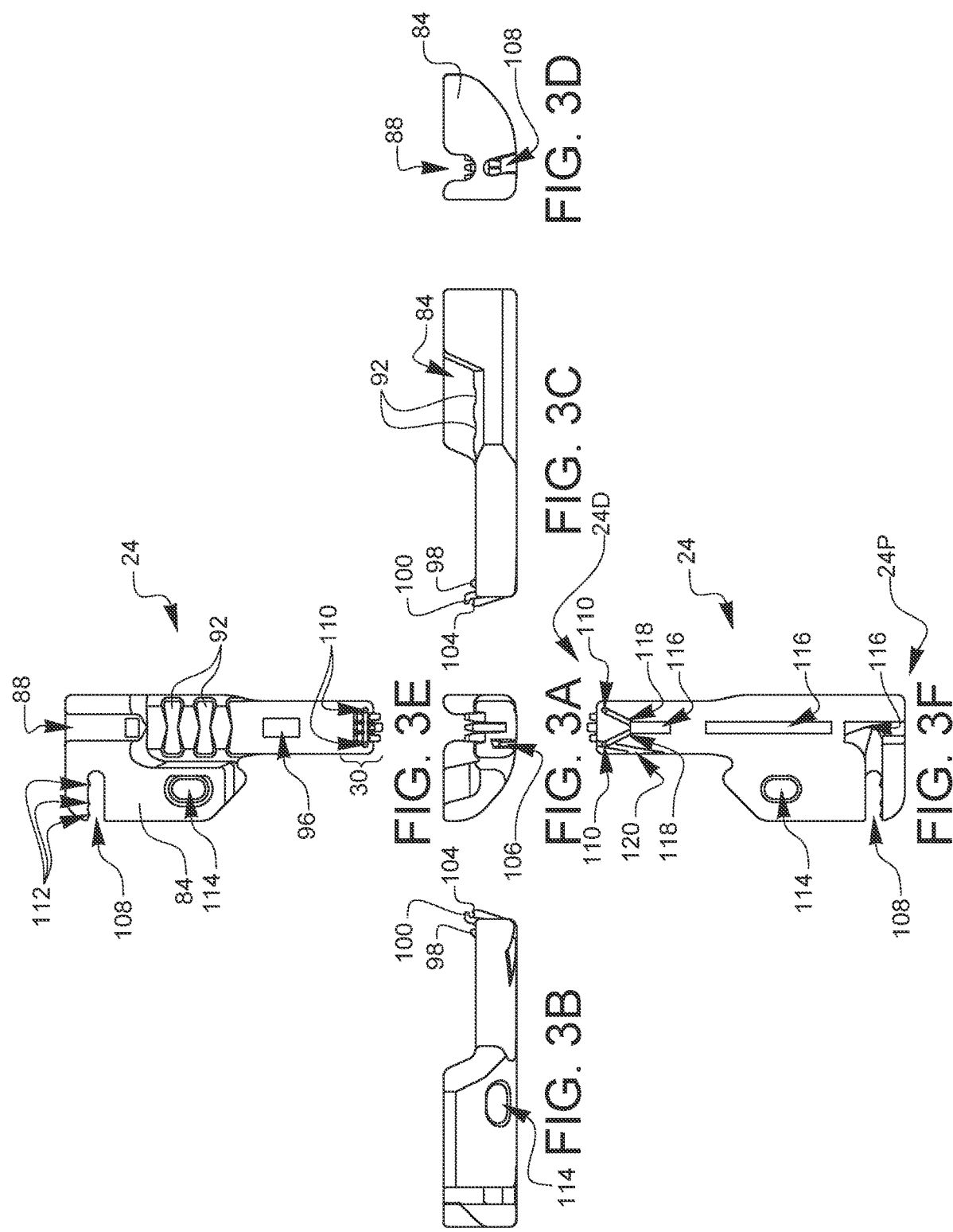

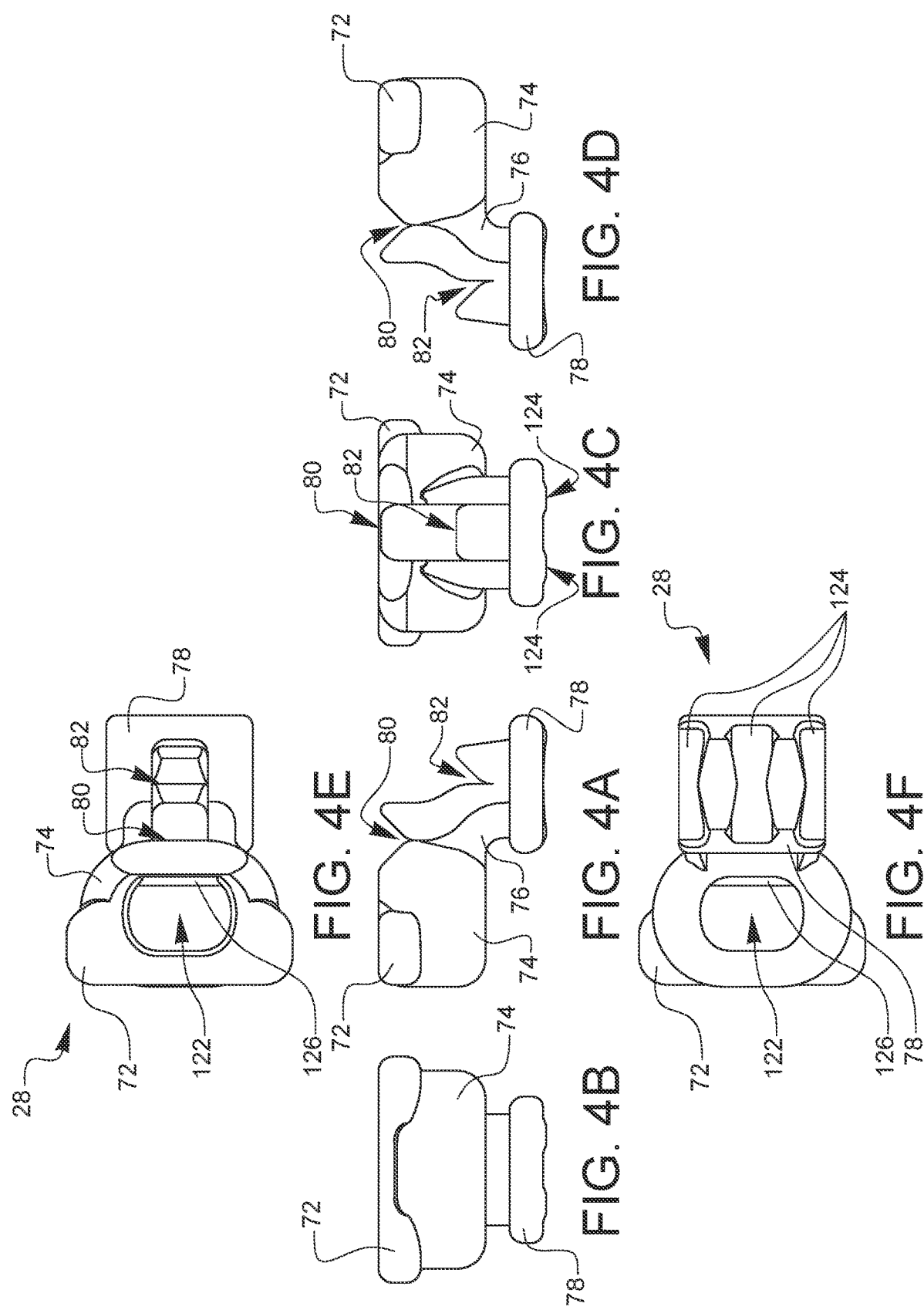

DEVICE FOR CARDIAC SURGERY

CROSS-REFERENCE TO RELATED APPLICATIONS

This application claims the benefit of U.S. Provisional Patent Application No. 63/219,011, filed Jul. 7, 2021, and U.S. Provisional Patent Application No. 63/219,017, filed Jul. 7, 2021, each of which is incorporated by reference herein in its entirety.

FIELD OF THE INVENTION

The claimed invention relates to minimally invasive cardiac surgical devices, and more specifically to a surgical device used in anastomosis during minimally invasive cardiac surgical procedures.

BACKGROUND

Minimally invasive surgical approaches are gaining increased interest in relation to coronary procedures. Coronary revascularization procedures such as the grafting of the internal thoracic artery (ITA) has shown superior long-term patency and improved patient outcome in coronary artery bypass graft (CABG) surgeries. While conventional approaches to ITA harvesting and grafting have included median sternotomy or multiple thoracoports, a minimally invasive approach is desirable. A minimally invasive procedure related to revascularization using either the left or right internal thoracic artery (ITA), or the left or right internal mammary artery (IMA) may utilize access to the ITAs via sub-xiphoid access, where increased surgical space is gained by accessing the internal thoracic arteries via incision at the subxiphocostal region.

Upon harvesting either the left internal thoracic artery (LITA) or the right internal thoracic artery (RITA) anastomoses to the left anterior descending (LAD) coronary artery and to the right coronary artery (RCA), respectively, can be performed without cardiopulmonary bypass (CPB). A significant advantage of this approach is that a perfectly harvested ITA graft can be perfectly anastomosed to the usual site on the LAD artery, or onto the RCA artery. A minimally invasive ITA harvesting procedure involving sub-xiphoid access also results in superior cosmetic results, is reasonably painless, and the arterial grafting can be accomplished on the beating heart. Recent approaches of minimally invasive ITA harvesting surgical techniques have been shown to result in increased effective length of ITA bypasses, reduced operation times, and improved patient recovery. These approaches, however, including all associated procedures, need to be minimally invasive if performed using a minimally invasive approach.

While less invasive surgical approaches for ITA harvesting and CABG have shown promise, the ability to conduct a CABG procedure without the use of CPB is highly desirable. Also, visualization, maintenance of insufflation, and distal suturing of a coronary anastomosis in totally endoscopic coronary artery bypass grafting on the beating heart is technically demanding. While minimally invasive surgical tools and procedures can create larger working spaces to accommodate additional surgical tools such as endoscopes, suturing tools, and the like, achieving an increased working space should ideally preserve chest wall integrity and avoid CPB. Likewise, a minimally invasive surgical approach should not compromise the reliability of a cardiac repair. Therefore, there is a need for improved minimally invasive surgical devices or procedures that contribute to facilitate improved efficacy and patency of minimally invasive coronary arty bypass grafting surgical procedures including anastomosis.

BRIEF DESCRIPTION OF THE DRAWINGS

FIGS. 3A, 3B, 3C, 3D, 3E, and 3F are front, left side, right side, rear, top, and bottom elevational views, respectively, of the pedestal of FIG. 1A.

FIGS. 4A, 4B, 4C, 4D, 4E, and 4F are front, left side, right side, rear, top, and bottom elevational views, respectively, of the retainer of FIG. 1A.

Figure 1:
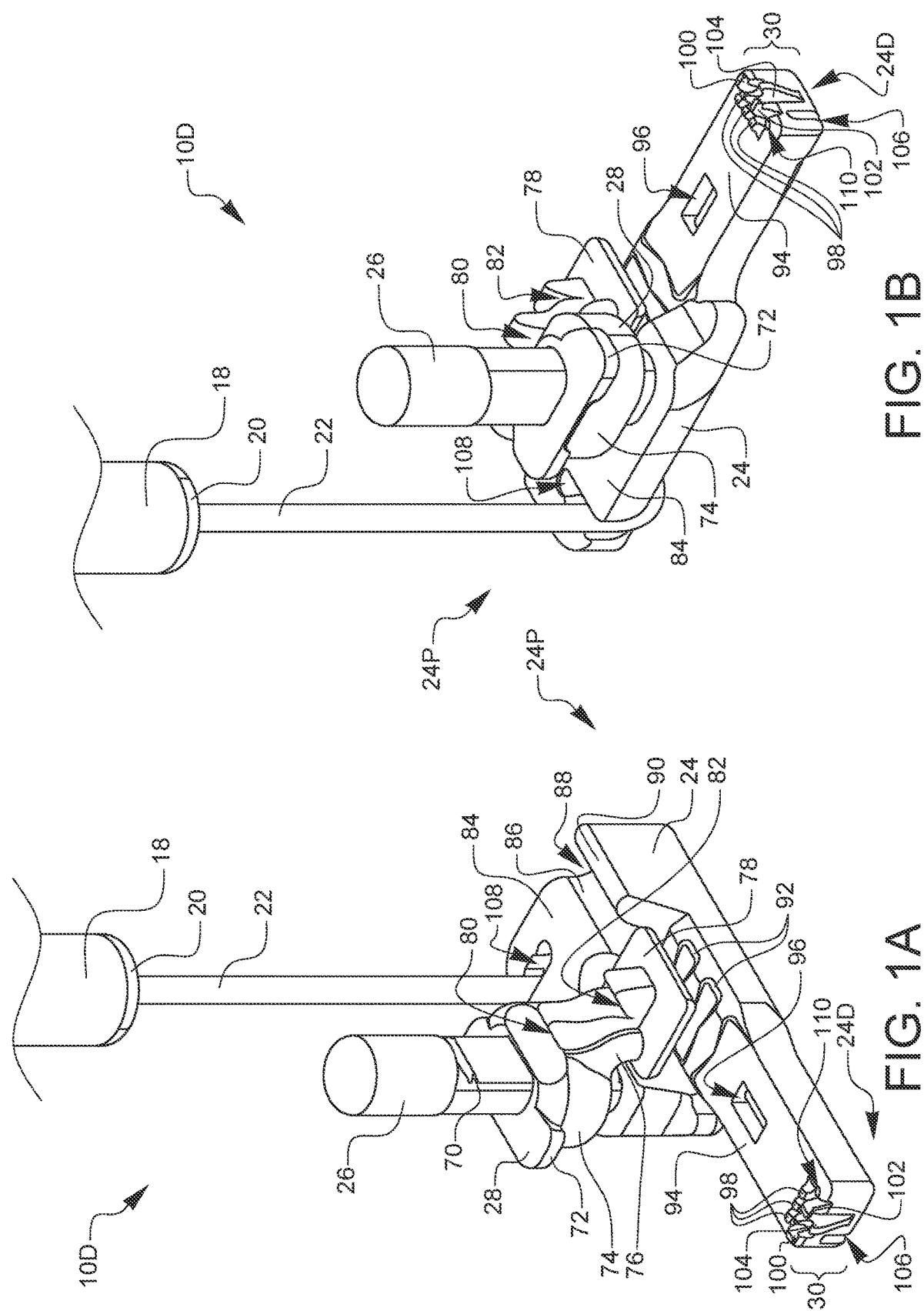
FIG. 1A is a top-right front perspective view of a distal end of the minimally invasive surgical device used in cardiac surgery.
FIG. 1B is a top-left-front perspective view of a distal end of the minimally invasive device used in cardiac surgery.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A is a top-right front perspective view of a distal end of the minimally invasive surgical device used in cardiac surgery. A distal end 10D of a device 10 used in minimally invasive cardiac surgery is illustrated. The device 10 has a sleeve 18 having a shaft tube 20 terminating in a hinge rod 22 which is coupled to a pedestal 24. At a proximal end 24P of the pedestal 24 a pedestal base 84, an inner wall 86, and an outer wall 90, are defined by the pedestal 24. The pedestal base 84 defines an articulation slot 108 which allows the hinge rod 22 to pass through and allows the pedestal 24 to be tilted from side to side for improved positioning during a minimally invasive surgical procedure. The inner wall 86 and the outer wall 90 further define a trough 88, in a direction parallel to a longitudinal axis of the pedestal 24 extending from the proximal end 24P to the distal end 24D of the pedestal 24. This trough 88 is configured to hold and guide a vessel in the pedestal 24 from the proximal end 24P towards the distal end 24D of the pedestal 24. The pedestal 24 also defines several textured surface elements 92 that are configured to help hold a vessel steady when loaded into the distal end 10D of the device 10 used in minimally invasive cardiac surgery. A stem 26 is fixedly attached to the pedestal 24. The stem 26 is largely cylindrical in shape but has a tooth 70 on one side. Other teeth may be located on the stem, but only one is visible here. While the stem 26 shown here is cylindrical, stems having other shapes, such as rectangular, or other holding features may be utilized by one skilled in the art. A soft retainer 28 is placed onto the stem 26 and is movably coupled to translate up and down in a vertical direction, although other movable configurations may be used as well. The soft retainer 28 further defines a collar or grip 72, a base 74, a jaw 76 extending from the base 74, and a planar member 78 at an end of the jaw 76. The jaw 76 of the soft retainer 28 also defines an upper détente 80 and a lower détente 82, which are configured to releasably hold suture or other filament for a temporary hold during a minimally invasive surgical procedure. The collar or grip 72 is configured to have a portion extending at least partially outside the base 74 of the soft retainer 28 The tooth 70 on the stem 26 is configured to releasably hold the soft retainer 28 in several designated vertical positions based on the vertical placement of the teeth. As configured here, the soft retainer 28 moves up and down relative to the pedestal 24. The planar member 78 of the soft retainer 28 contacts the pedestal 24 at a position where the textured surface elements 92 are located. These textured surface elements 92 and several corresponding textured elements on the planar member 78, not visible here, interface and combine to improve the grip onto a vessel held within the distal end 10D of the device 10.

The pedestal 24 also defines a suturing template 30 towards a distal end 24D of the pedestal 24. The suturing template 30 portion of the pedestal also defines a top surface 94 having a hole 96 passing therethrough. At the most distal end 24D of the pedestal 24, the suturing template 30 defines three indicating guides 98, a recess 106, a lower guide fin 104 and two upper guide fins, 100, 102 located on either side of the lower guide fin 104. The upper guide fins 100, 102 and the lower guide fin 104 are further towards the distal end 24D of the pedestal than the three guides 98. The upper guide fin 100 and upper guide fin 102 are shaped such that they alternate with the lower guide fin 104 and could entrain or temporarily hold or restrain a filament or suture across the suturing template 30 in a direction substantially perpendicular to an axis extending from the proximal end 24P to the distal end 24D of the pedestal 24. Adjacent to each upper guide fin 100, 102 are two suture channels 110 which communicate from the top surface 94 of the suturing template 30 to the underside of the suturing template 30 portion of the pedestal 24. These suture channels 110 and the upper guide fins 100, 102 and lower fin 104 are configured such that a suture could be directed from the underside of the pedestal 24, up through one of the suture channels 110, distally relative to upper guide fin 102, proximally relative to lower guide fin 104, distally relative to upper guide fin 100, and back through the opposite suture channels 110 adjacent to upper guide fin 100. It should be noted that other arrangements or suture routing could be employed in other embodiments. More details relating to these aforementioned features and suture pathways will be discussed later. FIG. 1B is a top-left-front perspective view of the distal end of the minimally invasive device used in cardiac surgery of FIG. 1A.

Figure 2:
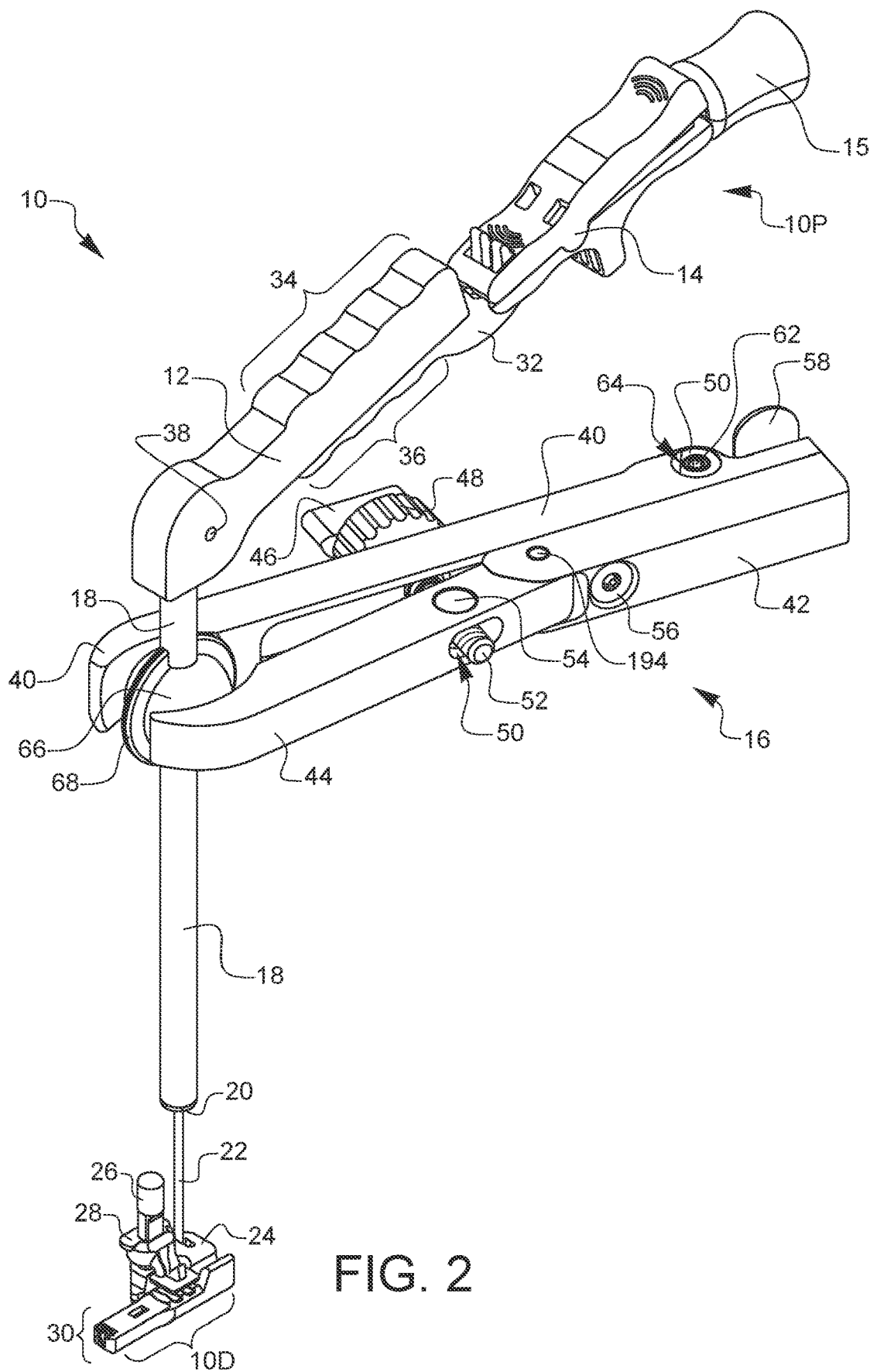
FIG. 2 is a top right front perspective view of the entire minimally invasive surgical device used in cardiac surgery of FIGS. 1A and 1B.

FIG. 2 is a top right front perspective view of the entire minimally invasive surgical device used in cardiac surgery of FIGS. 1A and 1B. FIG. 2 illustrates the entire device 10 in perspective view. At a proximal end 10P of the device 10, there is a suture locking apparatus 14 coupled to a lever arm 12. The lever arm 12 defines a grip 34 and has a lever 32 to which the suture locking apparatus 14 is directly coupled. The suture locking device 14 has a central conduit through which suture may pass and can be held fixedly within when engaged. The lever 32 has a grip 36 also, and the lever 32 is biased away from the lever arm 12 with a spring. There is a sleeve 18 coupled to the arm 12 which has an internal shaft tube 20 fixedly attached within. The sleeve 18 and shaft tube 20 terminate in a hinge rod 22 which is coupled to the distal end 10D of the device 10 at the pedestal 24. As previously described in regard to FIGS. 1A and 1B, the stem 26, soft retainer 28, and suturing template 30 of the distal end 10D of the device 10 are also shown here. The sleeve 18 also has a movable ball clamp 66 defining an equator 68 about its external surface. A clamp 16 is coupled to the ball clamp 66. The clamp 16 includes an upper clamp jaw 40, a clamp adapter 42, and a lower clamp jaw 44. The clamp adapter 42 is fixedly attached to the upper clamp jaw 40 by a screw 56 and the lower clamp jaw 44 is pivotably attached to the clamp adapter 42 by a pin 194 passed through the clamp adapter 42. The clamp 16 also has a thumb screw 46 having a thumb screw grip 48 and a thumb screw shaft 52 wherein the thumb screw shaft passes through both the upper clamp jaw 40 and the lower clamp jaw 44 through a gap 50 defined in the lower clamp jaw 44 in order to maintain a set tension between the upper clamp jaw 40 and the lower clamp jaw 44. It should be presumed that threading is present within the gap, but it is not visible in this view. The upper clamp jaw 40 and the lower clamp jaw 44, when clamped together as illustrated in FIG. 2, hold the ball clamp 66 in place. When the upper clamp jaw 40 and lower clamp jaw 44 are loosened, the ball clamp may still be held between the upper clamp jaw 40 and the lower clamp jaw 44, but the lowered compression of the ball clamp 66 along its equator 68 allow the two halves or segments of the ball clamp 66 delineated by the equator 68 to separate slightly. This renders the ball clamp 66 movable in a vertical direction along the sleeve 18 of the device 10. This also renders the ball clamp 66 and therefore the sleeve 18 pivotable in multiple orientations relative to the clamp 16 by allowing the ball clamp 66 to move freely within the jaws of the clamp 16 when the thumb screw 46 is loosened. While this structure is shown in FIG. 2, other methods and structures capable of clamping in a manner that allows for movement and adjustment of the distal end of a device such as the embodiments illustrated herein along several degrees of freedom such as the structure described here. A pull tab 15 is attached at a proximal end 10P of the entire device 10. The tab 15 is configured to securely hold a suture and pull the suture remotely from the proximal end 10P of the device 10 when necessary.

Further articulation of the device 10, in particular the distal end 10D of the device 10, can be achieved by squeezing or compressing the lever 32 towards the arm 12. When the lever 32 is squeezed towards the arm 12, and the arm 12 pivots around a pivot point 38, it defeats or limits a downward vertical compression on a smaller ball at the proximal end of the hinge rod 22, not shown in this view. When the lever 32 is squeezed towards the arm 12, the hinge rod 22 is pivotable and rotatable relative to the attachment point of the hinge rod 22 to the shaft tube 20. The downward vertical compression is the at rest configuration in the device 10 by biasing the lever 32 towards the arm 12 when not squeezed. The articulating rod, or articulating hinge rod provides a pivotable link useful in delivering and placing the distal end 10D of the device 10 to a specific targeted area for a surgical procedure.

FIGS. 3A, 3B, 3C, 3D, 3E, and 3F are front, left side, right side, rear, top, and bottom elevational views, respectively, of the pedestal of FIG. 1A. While the features of the pedestal 24 have already been described in regard to FIGS. 1A and 1B, additional features are visible in the elevational views. FIG. 3E illustrates a top view of the trough 88, the textured surface elements 92 and the template 30 including the location of the anchor suture channels 110, which defines the space on the pedestal 24 where a resected IMA may be held in place during a minimally invasive cardiac surgery. Also visible in FIG. 3E are several internal recesses 112 along the articulation slot 108 which can temporarily and releasably hold the pedestal 24 in place along several indexed positions with respect to the hinge rod. This permits the pedestal 24 to tilt side to side and be held in fixed positions along the pathway defined by the articulation slot 108. Also visible is the hole 114 through which the stem 26 can be inserted and fixedly attached to the pedestal 24. FIG. 3F illustrates the bottom of the pedestal 24 showing the location of the hinge rod channel 116 which passes from the proximal end 24P of the pedestal 24 towards the distal end 24D of the pedestal 24. The hinge rod channel 116 is discontinuous at the bottom surface but continues throughout the pedestal 24. Also illustrated are two suture channels 118 that communicate with the hinge rod channel 116 and through the pedestal 24 to the suture channels 110 on the top surface, as well as a side suture channel 120 branching off from one of the suture channels 110.

FIGS. 4A, 4B, 4C, 4D, 4E, and 4F are front, left side, right side, rear, top, and bottom elevational views, respectively, of the retainer of FIG. 1A. While the features of the soft retainer 28 have already been described in regard to FIGS. 1A and 1B, additional features are visible in the elevational views. The respective locations of the collar or grip 72, base 74, planar member 78, upper détente 80, and lower détente 82 are illustrated. Also shown are a central hole 122 for passing the stem 26 therethrough, several texture elements 124 on the bottom of the planar member 78, and a tab 126 in the central portion of the central hole 122. The tab 126 is configured to interface with one or more teeth on the stem 26 for the purpose of releasably holding the vertical position of the soft retainer 28 in place along the stem 26 when the entire device 10 is in use.

Figure 5A:
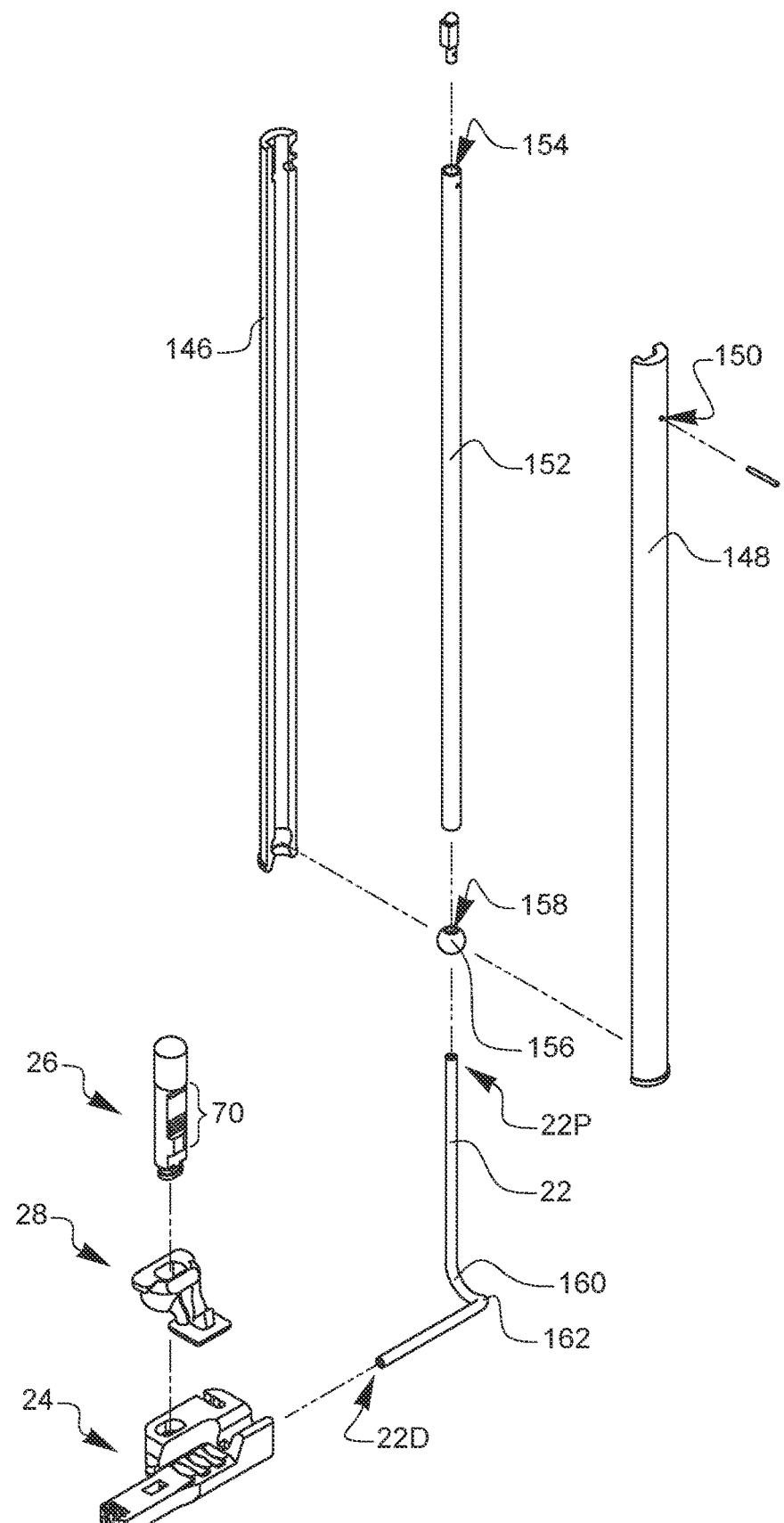
FIGS. 5A-5D are a series of exploded views illustrating assembly steps of the minimally invasive device used in cardiac surgery of FIG. 2.
Figure 5B:
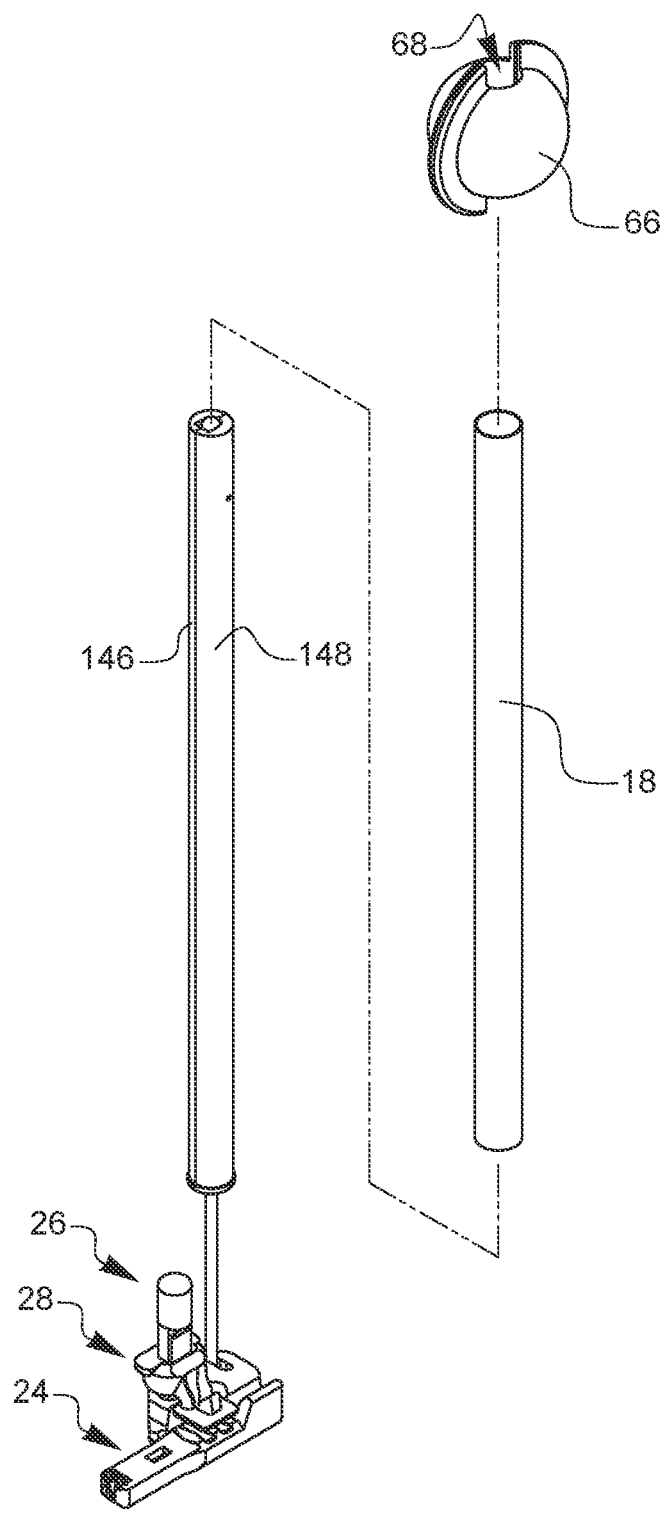

FIGS. 5A-5D are a series of exploded views illustrating assembly steps of the minimally invasive device used in cardiac surgery of FIG. 2. FIG. 5A illustrates the assembly of the device used in cardiac surgery of FIG. 2. Beginning with the pedestal 24, the stem 26 is inserted through the central hole 122 of the soft retainer 28 and into the hole 114 of the pedestal 24. The distal end 22D of the hinge rod 22 is inserted into the hinge rod channel 116 of the pedestal 24, which is not visible here, allowing for the proximal end 22P of the hinge rod 22 to pass into the articulation slot 108 of the pedestal 24. This is possible due to a first bend 160 and a second bend 162 along the length of the hinge rod 22. It should be noted that the hinge rod 22 is hollow and will allow filaments or suture to pass through the internal diameter of the hinge rod 22. A ball 156 having a center 158 is fixedly attached to the proximal end 22P of the hinge rod 22. A hole 154 is held against the ball 156 and a plunger 164 is inserted into a hole 154 of the inner tube 152. The plunger 164 has a protrusion 168. A first tube half 146 and a second tube half 148 are placed around the inner tube 152. It should be noted that both the first tube half 146 and second tube half 148 have recessed features 166, 167 to accommodate the ball 156 and the plunger 164 in the first tube half 146 and second tube half 148 without completely fixing their positions to or against the first tube half 146 or the second tube half 148. FIG. 5B illustrates the sleeve 18 being slid over the first tube half 146 and second tube half 148 such that the protrusion 168 of the plunger 164 still projects from within the center of the sleeve 18. Over the outside of the sleeve 18, the sleeve 18 is inserted into the center 210 of the movable ball clamp 66.

Figure 5C:
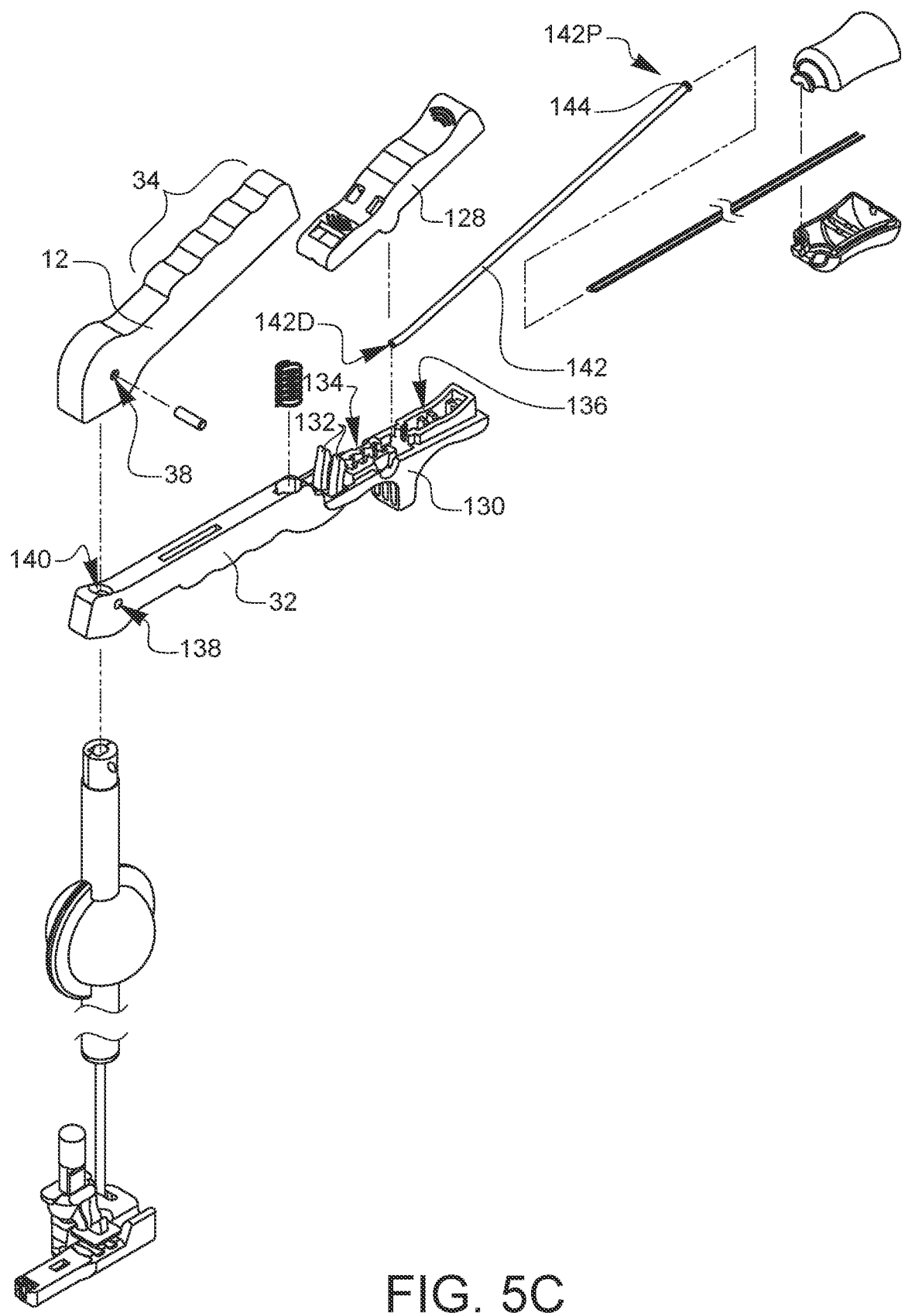

After the assembly steps illustrated in FIG. 5B, the end of the sleeve 18 with protrusion 168 projecting from the first tube half 146 and second tube half 148 has a channel 140 in lever 32 placed over the first tube half 146 and second tube half 148, as illustrated in FIG. 5C. The lever 32 also has a hole 138 on the side of the lever 32. A housing 130 is fixedly attached to a proximal end 32P of the lever 32. The lever arm 12, having a pivot point 38, is placed over the distal end 32D of lever 32. A pin 206 is placed in pivot point 38 and through hole 138 to hold the lever arm 12 permanently and pivotably onto the lever 32. A spring 214 is also fixedly attached within the lever 32 to maintain a bias of the arm 12 against the plunger 164. A suture tube 142 is placed into the housing 130, between the features of the tube gripping elements 134 and the suture gripping elements 136, with the proximal end 144 being held in a tube stop 145. A suture 212 is inserted into the proximal end 142P of the suture tube 142, down through the center of the lever 32, through the sleeve 18, hinge rod 22, and through to the distal end 24D of the pedestal 24. Finally, the first half 15A and the second half 15B of the pull tab 15 are closed over the two ends 212E of the suture 212. The pull tab 15 holds the suture firmly at the distal end of the device and can pull the suture 212 back through its described pathway through the entire device 10.

Figure 5D:
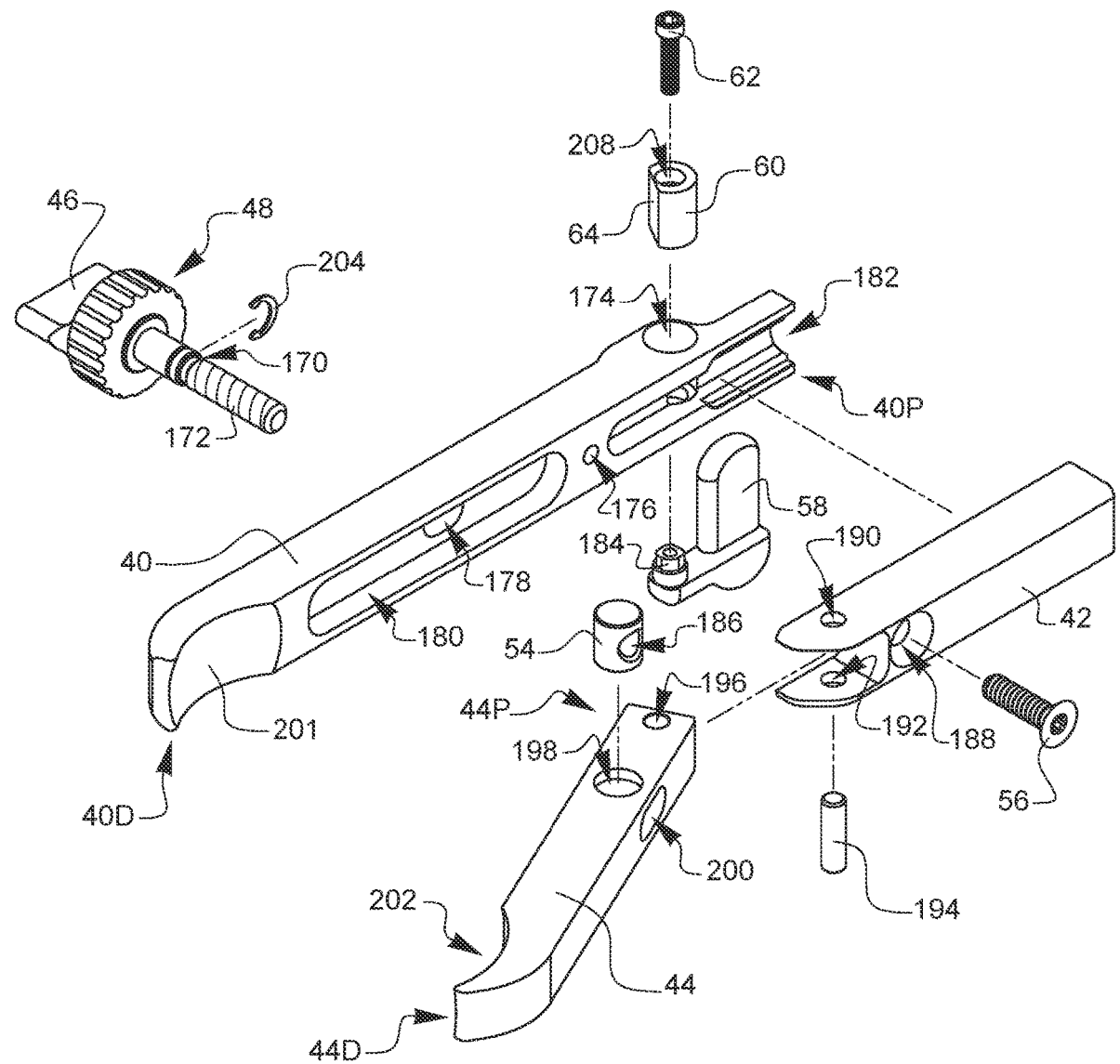

FIG. 5D shows some of the final assembly steps of the device 10 of FIG. 2. The upper clamp jaw 40 has an adapter channel 182 at its distal end 40D and also defines a hole 176, a recessed portion 180 with a hole 178. The lever lock 58 is inserted into a hole 174 on the upper clamp jaw 40. The lever lock 58 has a cam insert 184 that engages a hole 208 on the locking cam 60. The locking cam 60 also has a flat 64. A screw 62 is then inserted through the hole 208 and into a corresponding hole on the cam insert 184. The lower adapter clamp 42 is then mated with the upper clamp jaw 40. The upper clamp jaw 40 is mated with lower adapter clamp 42. The lower adapter clamp 42 further defines a hole 188, a top hole 190, and a bottom hole 192. The lower clamp jaw 44 further defines an end hole 196, a top hole 198, and a side hole 200. The lower clamp jaw 44 is inserted into the lower adapter clamp 42 with the end hole 196 aligned with the top hole 190 and the bottom hole 192 on the lower adapter clamp 42. A pin 194 is inserted into the bottom hole 192 through the hole 196 on the lower clamp jaw 44, and through the top hole 190 to fixedly and pivotably attach the lower clamp jaw 44 to the lower adapter clamp 42. The lower clamp jaw 44 also defines a curved jaw 202 at its distal end 44D. The barrel 54, having a center 186 is inserted into the top hole 198 on the lower clamp jaw 44. The adapter channel 182 and a corresponding channel on the lower adapter clamp 42 form a channel for inserting a surgical equipment holder and holding and positioning the clamp 16 portion of the overall entire device 10 onto a surgical equipment holder. The thumb screw 46 further defines a thumb screw grip 48 and a shaft 172. The shaft 172 has a recess 170. Once the thumb screw 46 is inserted into the hole 178 on the upper clamp jaw 40, a retaining ring 204 snaps into the recess 170 on the shaft 172, and then the shaft 172 is passed through the center 186 on the barrel 54 and finally through the side hole 200 on the lower clamp jaw 44. Tightening the thumb screw grip 48 into threads within the lower clamp jaw 44, which are not visible in this view, tightens the lower clamp jaw 44 relative to the upper clamp jaw 40 and closes the curved jaw 201 and the curved jaw 202 around the ball clamp 66, and also the ball clamp 66 around the sleeve 18 of the entire device 10.

Figure 6:
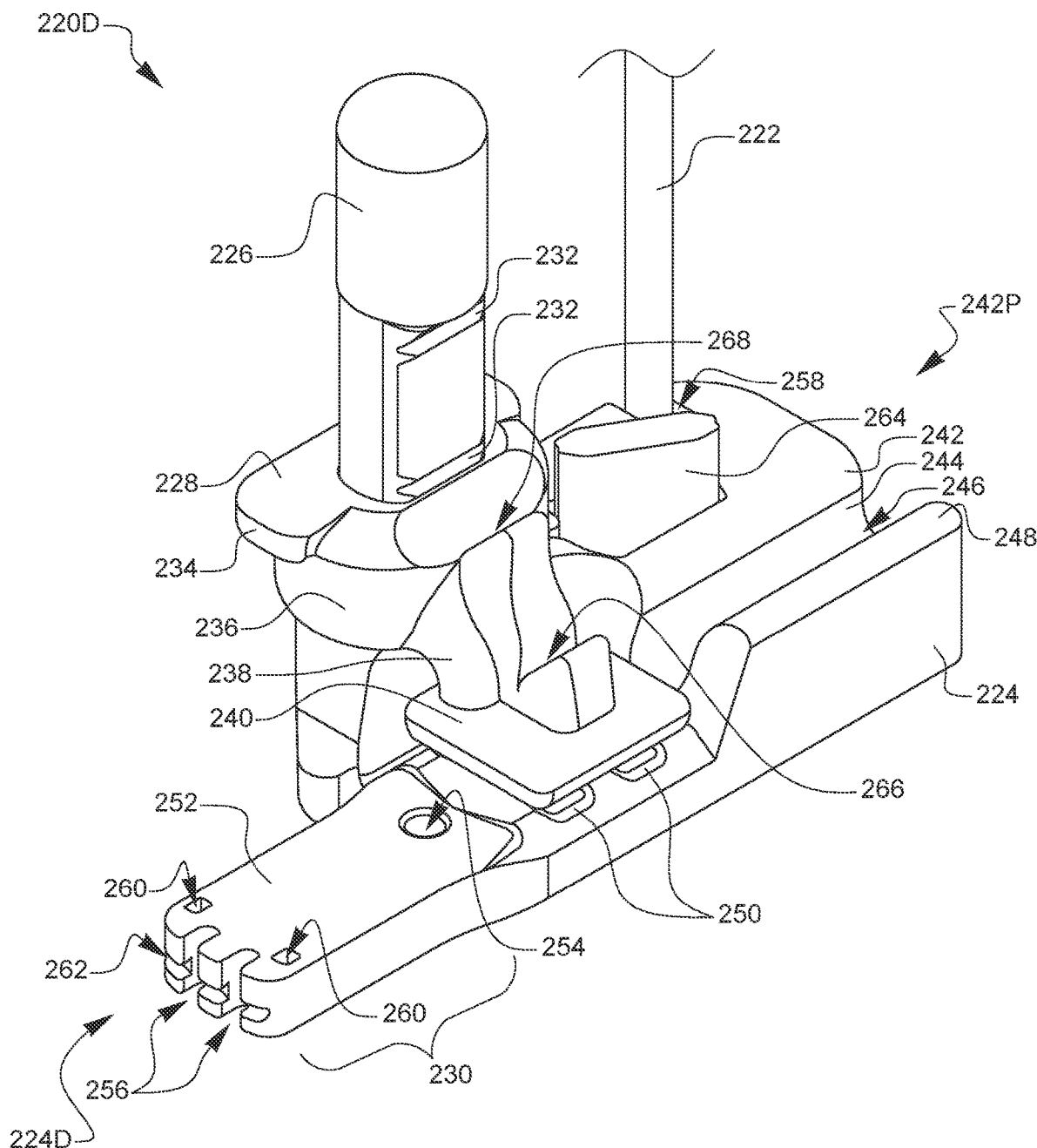
FIG. 6 is a top-left-front perspective view of a distal end of another embodiment of a minimally invasive surgical device used in cardiac surgery.

FIG. 6 is a top-right-front perspective view of a distal end of another embodiment of a minimally invasive surgical device used in cardiac surgery. A distal end 220D of a device 220 used in minimally invasive cardiac surgery is terminated in a hinge rod 222 which is coupled to a pedestal 224. A proximal end 224P of the pedestal 224 defines a pedestal base 242, an inner wall 244, and an outer wall 248. The pedestal base 242 also defines an articulation slot 258 which allows the hinge rod 222 to pass through and allows the pedestal 224 to be tilted from side to side for improved positioning during a minimally invasive surgical procedure. The inner wall 244 and the outer wall 248 further define a trough 246, in a direction parallel to a longitudinal axis of the pedestal 224 extending from the proximal end 224P to the distal end 224D of the pedestal 224. This trough 246 is configured to hold and guide a vessel in the pedestal 224 from the proximal end 224P towards the distal end 224D of the pedestal 224. The pedestal 224 also defines several textured surface elements 250 that are configured to help hold a vessel steady when loaded into the distal end 220D of the device 220 used in minimally invasive cardiac surgery. A stem 226 is fixedly attached to the pedestal 224. The stem 226 is largely cylindrical in shape but has a tooth 232 on one side. Additional teeth may be located on the stem, but only one is visible here. While the stem 226 shown here is cylindrical, stems having other shapes, such as rectangular, or other holding features may be utilized by one skilled in the art. A soft retainer 228 is placed onto the stem 226 and is movably coupled to translate up and down in a vertical direction, although other movable configurations may be used as well. The soft retainer 228 further defines a grip 234, a base 236, a jaw 238 extending from the base 236, and a planar member 240 at an end of the jaw 238. The grip 234 is extended beyond the base 236 of the soft retainer 228 to allow for a space or location to enable grasping with forceps or other surgical tools to aid vertical positioning of the soft retainer 228. The jaw 238 of the soft retainer 228 also defines an upper détente 268 and a lower détente 266, which are configured to releasably hold suture or other filament for a temporary hold during a minimally invasive surgical procedure. The tooth 232 on the stem 226 is configured to releasably hold the soft retainer 228 in several designated vertical positions based on the vertical placement of the teeth 232. As configured here, the soft retainer 228 moves up and down relative to the pedestal 224. The planar member 240 of the soft retainer 228 contacts the pedestal 224 at a position where the textured surface elements 250 are located. These textured surface elements 250 and several corresponding textured elements on the planar member 240, not visible here, interface and combine to improve the grip onto a vessel held within the distal end 220D of the device 220.

The pedestal 224 also defines a suturing template 230 towards a distal end 224D of the pedestal 224. The suturing template 230 portion of the pedestal also defines a top surface 252 having a hole 254 passing therethrough. At the most distal end 224D of the pedestal 224, the suturing template 230 defines several recesses 256 and a horizontal slot 262. The horizontal slot 262 may entrain or temporarily hold or restrain a filament of suture near the template 230 in a direction substantially perpendicular to an axis extending from the proximal end 224P to the distal end 224D of the pedestal 224. This suture, not shown here, would also span the recesses 256. The recesses 256 are configured to allow for the passage of a needle or suturing device to pass over or around a suture held in the horizontal slot 262. Adjacent to the distal end 224D of the pedestal 224 are two suture channels 260 which communicate from the top surface 252 of the suturing template 230 to the underside of the suturing template 230 portion of the pedestal 224. These suture channels 260, the horizontal slot 262, and the recesses 256 are configured such that a suture could be directed from the underside of the pedestal 224, up through one of the suture channels 260, horizontally through the horizontal slot 262 and the recesses 256, and back through the opposite suture channel 260. It should be noted that other arrangements or suture routing could be employed in other embodiments. More details relating to these aforementioned features and suture pathways will be discussed later.

Figure 7:
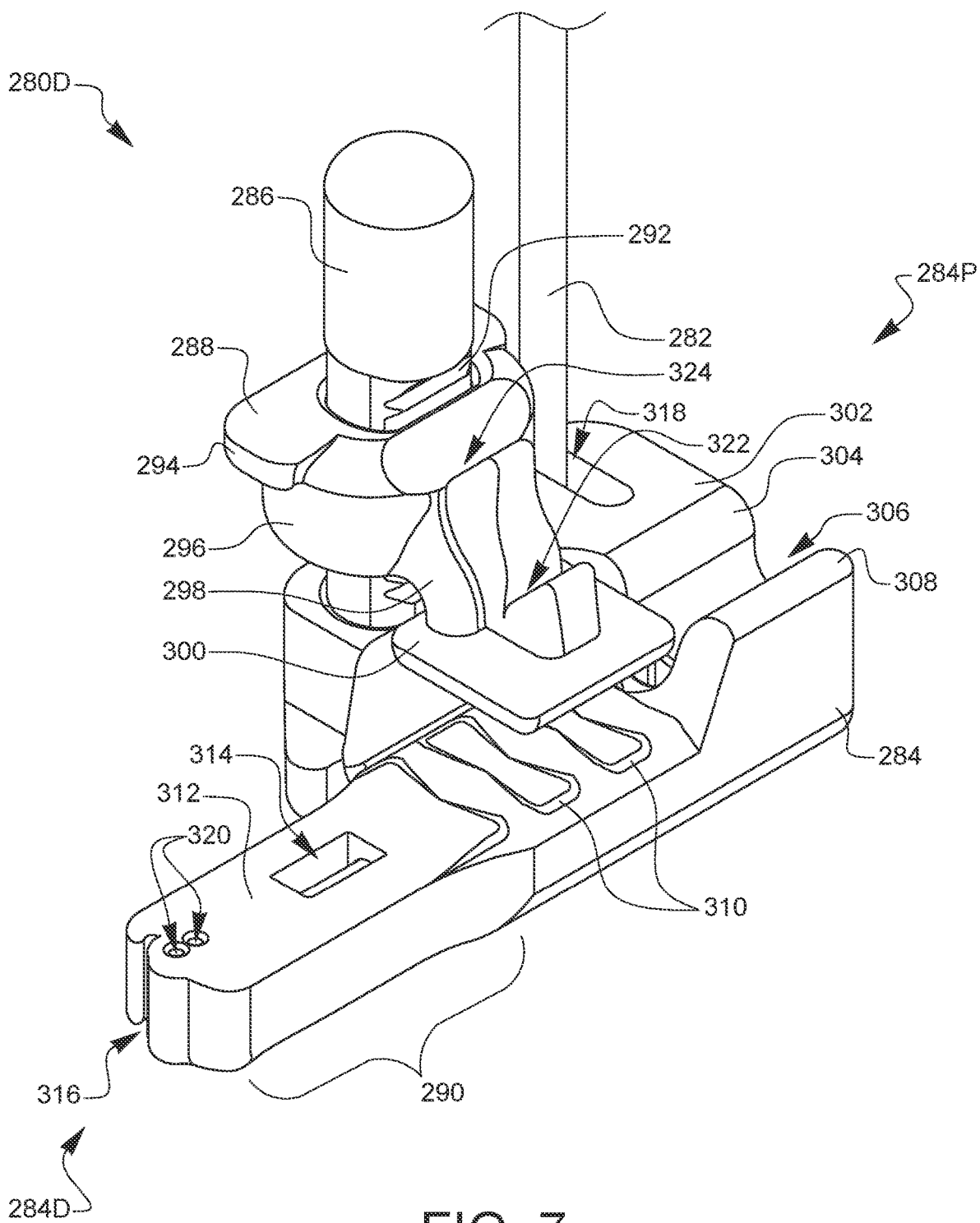
FIG. 7 is a top-left-front perspective of a distal end of another embodiment of a minimally invasive surgical device used in cardiac surgery.

FIG. 7 is a top-right-front perspective of a distal end of another embodiment of a minimally invasive surgical device used in cardiac surgery. A distal end 280D of a device 280 used in minimally invasive cardiac surgery is illustrated. The device 280 terminates in a hinge rod 282 which is coupled to a pedestal 284. At a proximal end 284P of the pedestal 284 a pedestal base 302, an inner wall 304, and an outer wall 308, are defined by the pedestal 284. The pedestal base 302 also defines an articulation slot 318 which allows the hinge rod 282 to pass through and allows the pedestal 284 to be tilted from side to side for improved positioning during a minimally invasive surgical procedure. The inner wall 304 and the outer wall 308 further define a trough 306, in a direction parallel to a longitudinal axis of the pedestal 284 extending from the proximal end 284P to the distal end 284D of the pedestal 284. This trough 306 is configured to hold and guide a vessel in the pedestal 284 from the proximal end 284P towards the distal end 284D of the pedestal 284. The pedestal 284 also defines several textured surface elements 310 that are configured to help hold a vessel steady when loaded into the distal end 280D of the device 280 used in minimally invasive cardiac surgery. A stem 286 is fixedly attached to the pedestal 284. The stem 286 is largely cylindrical in shape but has a tooth 292 on one side. Other teeth may be located on the stem, but only one is visible here. While the stem 286 shown here is cylindrical, stems having other shapes, such as rectangular, or other holding features may be utilized by one skilled in the art. A soft retainer 288 is placed onto the stem 286 and is movably coupled to translate up and down in a vertical direction, although other movable configurations may be used as well. The soft retainer 288 further defines a grip 294, a base 296, a jaw 298 extending from the base 296, and a planar member 300 at an end of the jaw 298. The soft retainer is configured similarly to other previously described embodiments. The jaw 298 of the soft retainer 288 also defines an upper détente 324 and a lower détente 322, which are configured to releasably hold suture or other filament for a temporary hold during a minimally invasive surgical procedure. The tooth 292 on the stem 286 is configured to releasably hold the soft retainer 288 in several designated vertical positions based on the vertical placement of the teeth. As configured here, the soft retainer 288 moves up and down relative to the pedestal 284. The planar member 300 of the soft retainer 288 contacts the pedestal 284 at a position where the textured surface elements 310 are located. These textured surface elements 310 and several corresponding textured elements on the planar member 300, not visible here, interface and combine to improve the grip onto a vessel held within the distal end 280D of the device 280.

The pedestal 284 also defines a suturing template 290 towards a distal end 284D of the pedestal 284. The suturing template 290 portion of the pedestal also defines a top surface 312 having a hole 314 passing therethrough. At the most distal end 284D of the pedestal 284, the suturing template 290 defines a recess 316 as well as two suture channels adjacent to the recess 316 which communicate from the top surface 312 of the suturing template 290 to the underside of the suturing template 290 portion of the pedestal 284. It should be noted that other arrangements or suture routing could be employed in other embodiments. More details relating to these aforementioned features and suture pathways will be discussed later.

Figure 8:
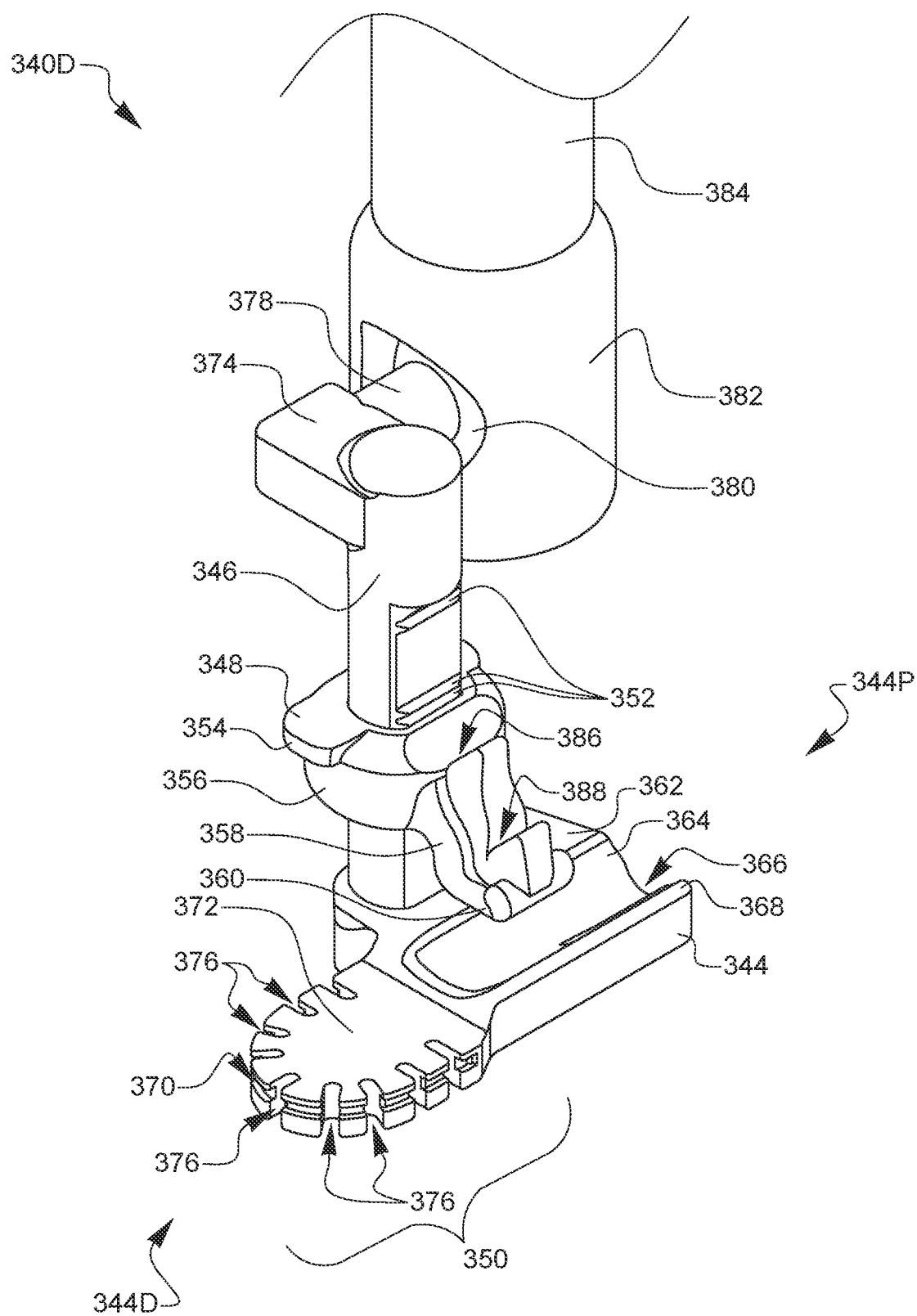
FIG. 8 is a top-left-front perspective of a distal end of another embodiment of a minimally invasive surgical device used in cardiac surgery.

FIG. 8 is a top-left-front perspective of a distal end of another embodiment of a minimally invasive surgical device used in cardiac surgery. A distal end 340D of a device 340 used in minimally invasive cardiac surgery is illustrated. The device 340 terminates in a shaft 384 having a holding portion 382 holding an articulating 380 which is connected to a smaller shaft segment 378 terminating in a mount 374. The mount 374 is connected to a stem 346, which is connected to a pedestal base 362 of a pedestal 344. At a proximal end 344P of the pedestal 344 the pedestal base 362, an inner wall 364, and an outer wall 368, are defined by the pedestal 344. Movement of the stem 346 by way of connection to the articulation ball 380 allows the pedestal 344 to be tilted from side to side for improved positioning during a minimally invasive surgical procedure. The inner wall 364 and the outer wall 368 further define a trough 366, in a direction parallel to a longitudinal axis of the pedestal 344 extending from the proximal end 344P to the distal end 344D of the pedestal 344. This trough 366 is configured to hold and guide a vessel in the pedestal 344 from the proximal end 344P towards the distal end 344D of the pedestal 344. The stem 346 is fixedly attached to the pedestal 344. The stem 346 is largely cylindrical in shape but has several 352 on one side. Other teeth may be located on the stem, but only three are visible here. While the stem 346 shown here is cylindrical, stems having other shapes, such as rectangular, or other holding features may be utilized by one skilled in the art. A soft retainer 348, which is similar to other embodiments described herein, is placed onto the stem 346 and is movably coupled to translate up and down in a vertical direction, although other movable configurations may be used as well. The soft retainer 348 further defines a grip 354, a base 356, a jaw 358 extending from the base 356, and a planar member 360 at an end of the jaw 358. The jaw 358 of the soft retainer 348 also defines an upper détente 386 and a lower détente 388, which are configured to releasably hold suture or other filament for a temporary hold during a minimally invasive surgical procedure. The teeth 352 on the stem 346 are configured to releasably hold the soft retainer 348 in several designated vertical positions based on the vertical placement of the teeth. As configured here, the soft retainer 348 moves up and down relative to the pedestal 344. The planar member 360 of the soft retainer 348 contacts the pedestal 344 at a position where a vessel might be held. The soft retainer and the trough 366 interface and combine to improve the grip onto a vessel held within the distal end 340D of the device 340.

The pedestal 344 also defines a suturing template 350 towards a distal end 344D of the pedestal 344. The suturing template 350 portion of the pedestal also defines a top surface 372. Around the distal end 344D of the pedestal 344, the suturing template 350 defines several recesses 376 and a horizontal slot 370 placed around the distal end 344D of the pedestal 344. The recess 376 and horizontal slot 370 are configured such that could entrain or temporarily hold or restrain a filament or suture across the suturing template 350 in a direction substantially perpendicular to an axis extending from the proximal end 344P to the distal end 344D of the pedestal 344. More details relating to these aforementioned features and suture pathways will be discussed later.

Figure 9:
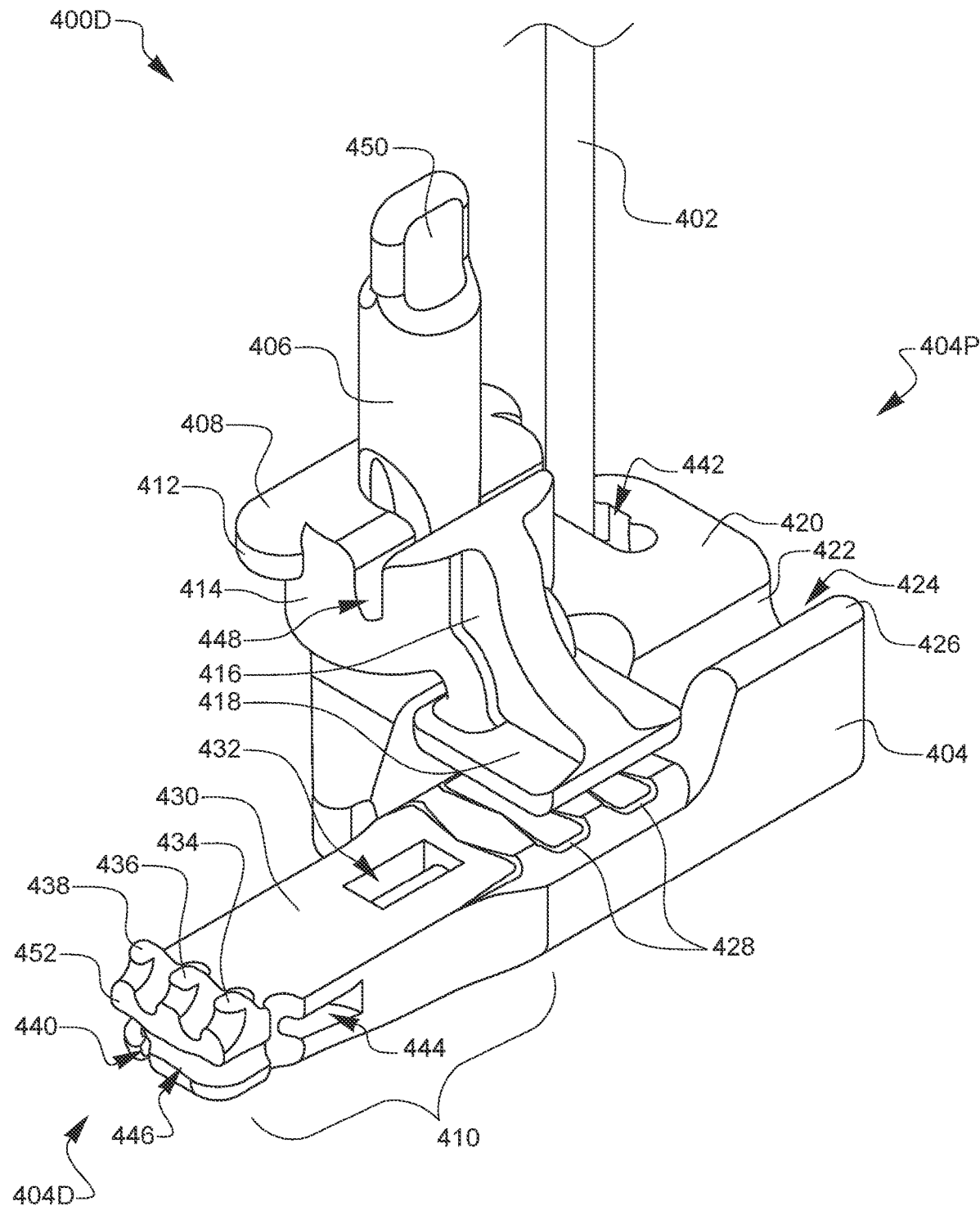
FIG. 9 is a top-left-front perspective of a distal end of another embodiment of a minimally invasive surgical device used in cardiac surgery.

FIG. 9 is a top-left-front perspective of a distal end of another embodiment of a minimally invasive surgical device used in cardiac surgery. A distal end 400D of a device 400 used in minimally invasive cardiac surgery is illustrated. The device 400 terminates in a hinge rod 402 which is coupled to a pedestal 404. At a proximal end 404P of the pedestal 404 a pedestal base 420, an inner wall 422, and an outer wall 426, are defined by the pedestal 404. The pedestal base 420 defines an articulation slot 442 which allows the hinge rod 402 to pass through in such a manner that it allows the pedestal 404 to be tilted from side to side for improved positioning during a minimally invasive surgical procedure. The inner wall 422 and the outer wall 426 further define a trough 424, in a direction parallel to a longitudinal axis of the pedestal 404 extending from the proximal end 404P to the distal end 404D of the pedestal 404. This trough 424 is configured to hold and guide a vessel in the pedestal 404 from the proximal end 404P towards the distal end 404D of the pedestal 404. The pedestal 404 also defines several textured surface elements 428 that are configured to help hold a vessel steady when loaded into the distal end 400D of the device 400 used in minimally invasive cardiac surgery. A stem 406 is fixedly attached to the pedestal 404. The stem 406 is largely cylindrical in shape but has a tooth on one side, which is not visible here. Other teeth may be located on the stem in alternate embodiments. While the stem 406 shown here is cylindrical, stems having other shapes, such as rectangular, or other holding features may be utilized by one skilled in the art. A soft retainer 408 is placed onto the stem 406 and is movably coupled to translate up and down in a vertical direction, although other movable configurations may be used as well. The soft retainer 408 further defines a grip 412 as described in regard to other embodiments, a base 414, a jaw 416 extending from the base 414, and a planar member 418 at an end of the jaw 416. The jaw 416 of the soft retainer 408 also defines an upper détente 448, which is configured to releasably hold suture or other filament for a temporary hold during a minimally invasive surgical procedure. As configured here, the soft retainer 408 moves up and down relative to the pedestal 404. The planar member 418 of the soft retainer 408 contacts the pedestal 404 at a position where the textured surface elements 428 are located. These textured surface elements 428 and several corresponding textured elements on the planar member 418, not visible here, interface and combine to improve the grip onto a vessel held within the distal end 400D of the device 400.

The pedestal 404 also defines a suturing template 410 towards a distal end 404D of the pedestal 404. The suturing template 410 portion of the pedestal also defines a top surface 430 having a hole 432 passing therethrough. At the most distal end 404D of the pedestal 404, the suturing template 410 defines a recess 440, a horizontal slot 446, and three fins 434, 436, 438. The fins 434, 436, 438 are adjacent to the distal end 404D of the pedestal 404. The fins 434, 436, 438 are shaped such that they could entrain or temporarily hold or restrain a filament or suture across the suturing template 410 in a direction substantially perpendicular to an axis extending from the proximal end 404P to the distal end 404D of the pedestal 404. Adjacent to the fins 434, 436, 438 are two suture channels 444 which communicate from the distal end 404D of the pedestal 404 to the underside of the suturing template 410 portion of the pedestal 404. These suture channels 444 and the fins 434, 436, 438 are configured such that a suture could be directed from the underside of the pedestal 404, up through one of the suture channels 444, and around the various features of the suturing template 410. It should be noted that other arrangements or suture routing could be employed in other embodiments. More details relating to these aforementioned features and suture pathways will be discussed later.

Figure 10:
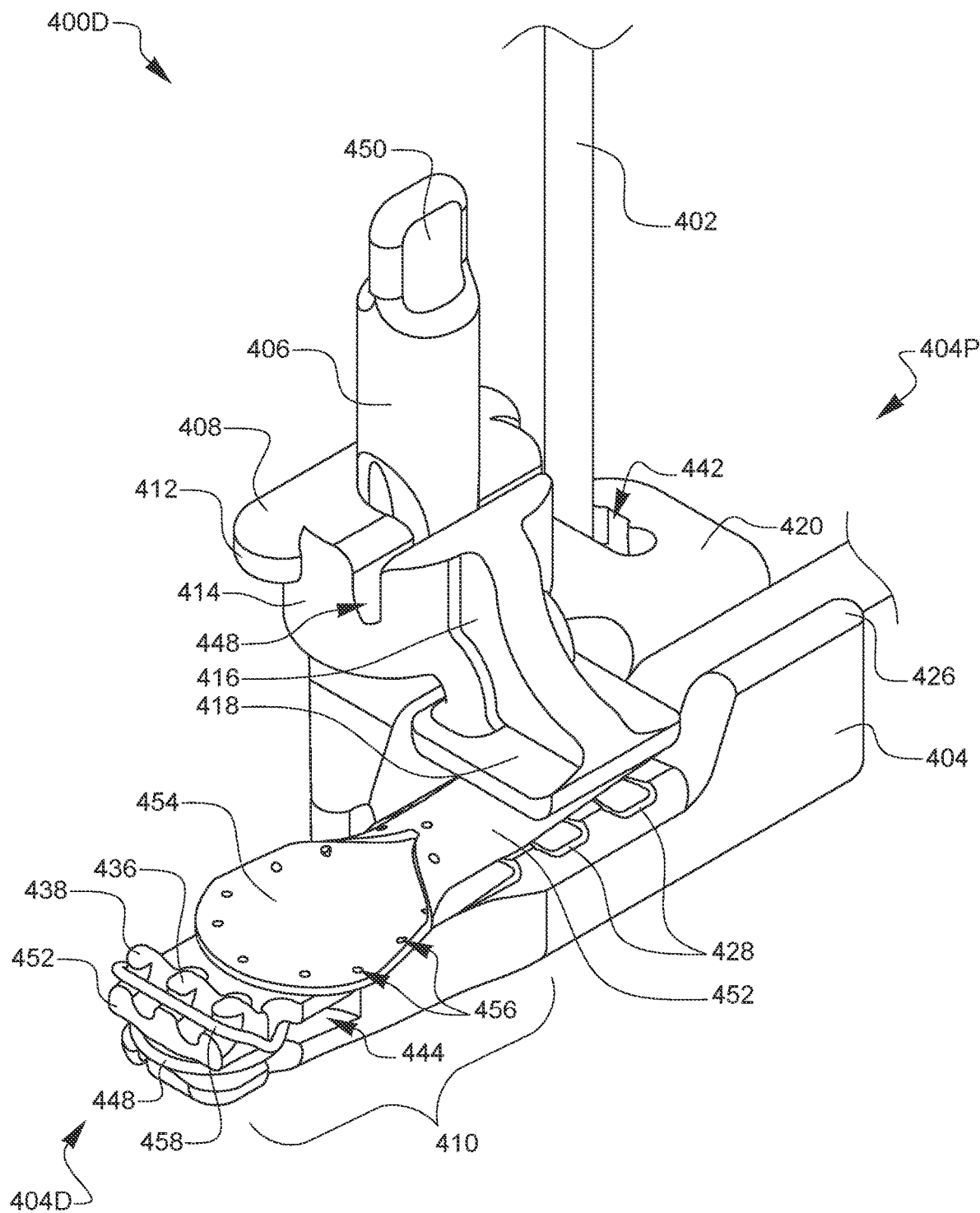
FIG. 10 is a top-left-front perspective of the distal end of the embodiment of a minimally invasive surgical device of FIG. 9.

FIG. 10 is a top-left-front perspective of the distal end of the embodiment of a minimally invasive surgical device of FIG. 9. FIG. 10 shows the distal end 400D of the device 400 with a vessel 452 held between the planar member 418 on the soft retainer 408 and the surface 430 of the pedestal 404. The vessel 452 is held in the trough 424 and terminates in a prepared "cobra head" 454 end of the vessel 452. The cobra head 454 is so named due to its resemblance to the head of a cobra. The arrangement of the vessel 452 illustrated in FIG. 10 is demonstrative of the manner in which the device 400 would hold or stabilize a vessel 452 during an anastomosis procedure as part of a minimally invasive CABG operation. Several suturing site indicators are noted on the cobra head 454 of the vessel 452, indicating ideal locations of suture placement during the grafting of the vessel 452. Also illustrated in FIG. 10 is the placement of a guide suture 458. The guide suture 458 can help the surgeon by guiding and holding stitches during the anastomosis procedure, keeping the stitching operations tangle free and organized.

Figure 11:
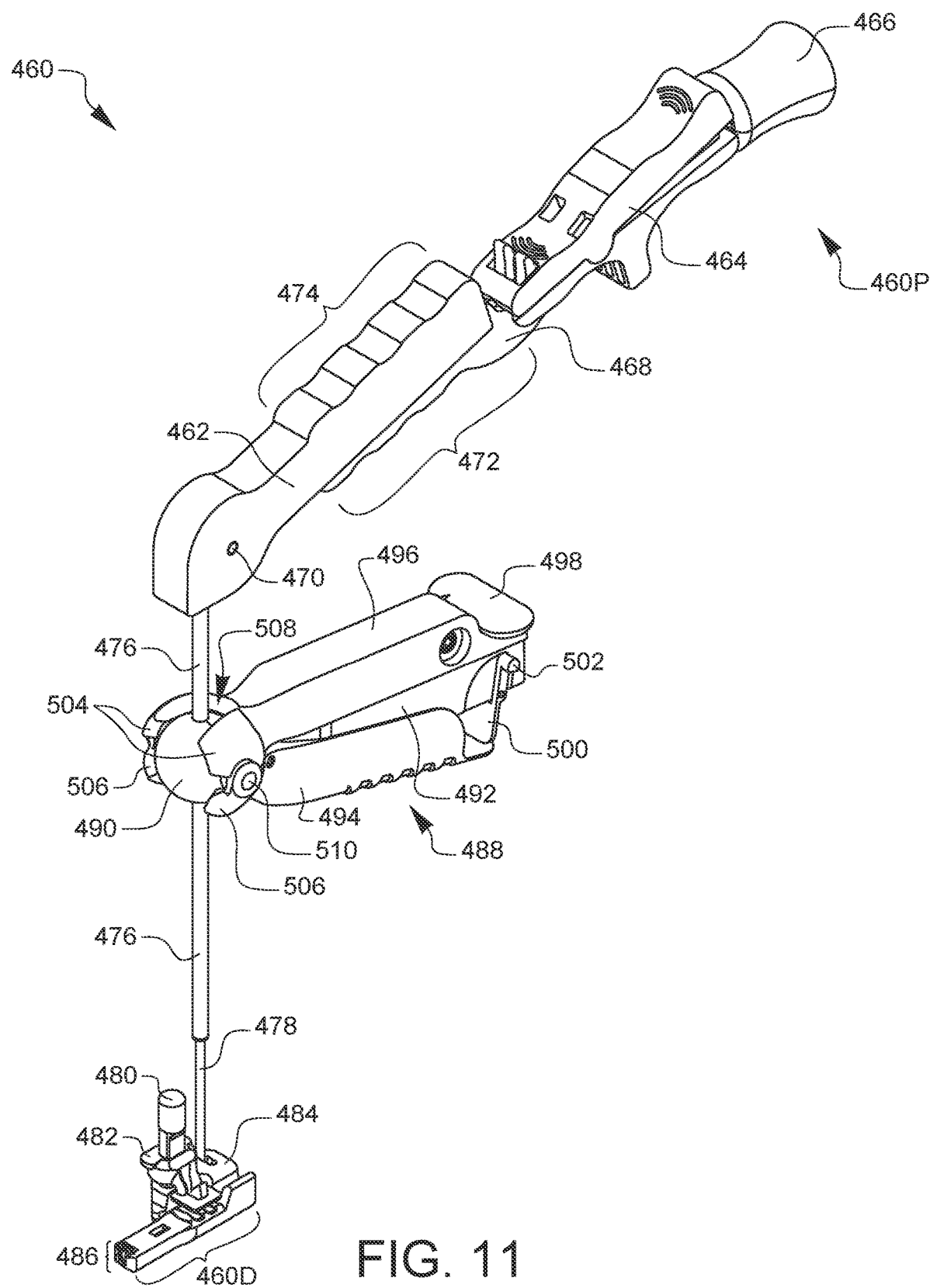
FIG. 11 is a top right front perspective view of another embodiment of a minimally invasive surgical device used in cardiac surgery.

FIG. 11 is a top right front perspective view of another embodiment of a minimally invasive surgical device used in cardiac surgery. FIG. 11 is a top right front perspective view of another embodiment of an entire minimally invasive surgical device used in cardiac surgery. FIG. 11 illustrates the entire device 460 in perspective view, the device 460 having an alternate clamping system. At a proximal end 460P of the device 460, there is a suture locking apparatus 464 coupled to a lever arm 462. The lever arm 462 defines a grip 474 and has a lever 468 to which the suture locking apparatus 464 is directly coupled. The lever 468 has a grip 36 also, and the lever 468 is biased away from the lever arm 462 with a spring. There is a sleeve 476 coupled to the arm 462 which has an internal shaft tube, not visible here, fixedly attached within. The sleeve 476 and shaft tube terminate in a hinge rod 478 which is coupled to the distal end 460D of the device 460 at the pedestal 484. As previously described in regard to FIGS. 1A and 1B, the stem 480, soft retainer 482, and suturing template 486 of the distal end 460D of the device 460 are also shown here. The sleeve 476 also has a movable spherical anchor 490, some details of which will be described later. This spherical anchor clamping system includes a spherical clamp 488 coupled to the spherical anchor 490. The clamp 488 includes a clamp base 496 attached to a base 492, and a lever 494 pivotably coupled to the clamp base 496. The clamp base 496 has an upper partial spherical clamp jaw 504 having a recess 508 and the lever 494 has a lower partial spherical clamp jaw 506 which also has a recess, not visible in this view. The clamp base 496 also includes an adapter end, not visible here, for attachment to a surgical equipment holder as previously described herein. The adapter end of the clamp base 496 can be locked onto a surgical equipment holder by engaging a lever lock 498, which is pivotably attached to the end of the clamp base 496. The base 492 also has an interference latch 500 which defines a latch guide 502 which can be rotated to serve as an interference once the spherical anchor clamp 488 is released to prevent the spherical anchor clamp 488 from being unintentionally squeezed and allowing the movable spherical anchor 490 to move along the sleeve 476 of the device 460. The spherical anchor clamp 488 can be squeezed by moving the lever 494 closer to the clamp base 496. The lever 494 is normally biased away from the clamp base 496 by a spring, which brings the upper partial spherical clamp jaw 504 and the lower partial spherical clamp jaw 506 closer together by pivoting around a pin 510, thereby compressing the movable spherical anchor 490 and preventing it from moving along the sleeve 476. This biasing spring is not illustrated here but will be described in more detail later. Another feature of the spherical anchor clamp 488 is the two partial spherical clamp jaws 504, 506. This feature of the partial spherical clamp jaws 504, 506 is to allow for the sleeve 476 of the device 460 to pass through the spherical anchor clamp 488 and the spherical anchor 490, but still be clamped from a substantially perpendicular or transverse direction with respect to a longitudinal axis of the sleeve. The sleeve 476 can still be pivoted or swiveled to some extent within the spherical anchor clamp 488, but the motion of the sleeve 476 is limited by the boundaries formed by the recesses 508 of the partial spherical clamp jaws 504, 506. There is also, not entirely shown in this view, a split in the movable spherical anchor 490. When the upper partial spherical clamp jaw 40 and lower partial spherical clamp jaw 44 are positioned away from one another, the spherical anchor 490 may still be held between the upper partial spherical clamp jaw 40 and the lower partial spherical clamp jaw 44, but the lowered force on the movable spherical anchor 490 along its equator allow the two halves of the spherical anchor 490 delineated by the equator to separate slightly. This renders the movable spherical anchor 490 movable in a vertical direction along the sleeve 476 of the device 460. This also renders the spherical anchor 490 and also the sleeve 476 pivotable in multiple orientations relative to the spherical anchor clamp 488 by allowing the spherical anchor 490 to move freely within the partial spherical clamp jaws 504, 506 of the spherical anchor clamp 488 when the spherical anchor clamp 488 is loosened. Some embodiments of the spherical anchor 490 may also have partial or complete circumferential protrusions around the external surface of the spherical anchor. These protrusions can provide a motion limiting feature when engaged with the recesses of one or both of the partial spherical clamp jaws of the spherical anchor clamp 488. While this structure is shown in FIG. 11, other methods and structures capable of clamping in a manner that allows for movement and adjustment of the distal end of a device such as the embodiments illustrated herein along several degrees of freedom such as the structure described here. A pull tab 466 is also attached at a proximal end 460P of the device 460. The tab 466 is configured to securely hold a suture and pull the suture remotely from the proximal end 460P of the device 460 when necessary.

Further articulation of the device 460, in particular the distal end 460D of the device 460, can be achieved by squeezing or compressing the lever 468 towards the arm 462. When the lever 468 is squeezed towards the arm 462, and the arm 462 pivots around a pivot point 470, it defeats or limits a downward vertical compression on a smaller ball at the proximal end of the hinge rod 478, not shown in this view but previously described. When the lever 468 is squeezed towards the arm 462, the hinge rod 478 is pivotable and rotatable relative to the attachment point of the hinge rod 478 to the shaft tube which is not shown in this view. The downward vertical compression is the at rest configuration in the device 460 by biasing the lever 468 away from the arm 462 when it is not squeezed.

Figure 12:
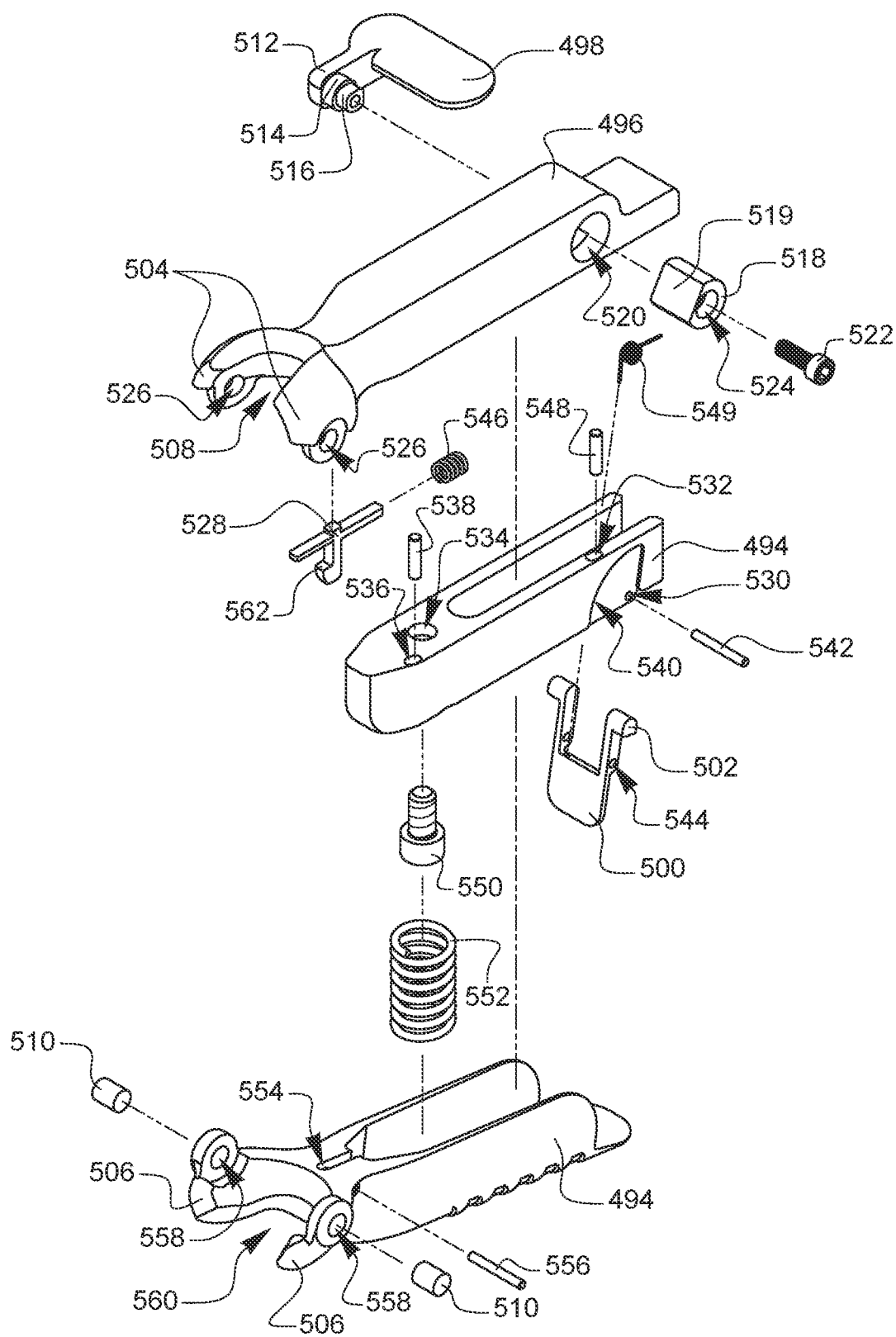
FIG. 12 is an exploded view of a spherical anchor clamp used in the minimally invasive surgical device of FIG. 11.

FIG. 12 is an exploded view of a spherical anchor clamp system used in the minimally invasive surgical device of FIG. 11. The clamp base 496 defines a hole 520 into which a lever lock 498 is inserted. The lever lock 498 further defines a lever lock shaft 514 terminating in a lever lock insert 516. The lever lock insert 516 is configured to interface and connect to a hole 524 on a locking cam 518. The locking cam 518 also defines a cam flat 519 that is configured to engage and releasably lock into an instrument attachment end on a surgical equipment holder. The locking cam 518 and the lever lock 498 are movably attached to the clamp base 496 with the use of a screw 522, although alternative means of attachment known to one skilled in the art may also be used. Next, the clamp base 496 is placed onto the base 492 and aligned using two pins 538, 548 which are inserted into two holes 536, 532, respectively, which are defined by the base 492 to align the base 492 to the clamp base 496. The base 492 is fixedly attached to the clamp base 496 with the use of a screw 550, although alternate means of attachment known to one skilled in the art may also be used. A latch 500 having a latch guide 502 an outer hole 544, and a spring guide hole 545 is placed over the base 492 and into a latch recess 540 defined by the base 492. The latch recess 540 effectively limits the travel of the latch 500 between a substantially horizontal position and a substantially vertical position. The movement and configuration of the latch 500 will be described later. A spring 549 is placed within an inner instrument adapter channel 495 of the base 492 and into a hole 545 of the latch 500 and is biased against the bottom of the clamp base 496 when assembled. The latch 500 is held in place by the insertion of a latch pin 542 first into hole 530 on the base 492, into corresponding hole 544 on the latch 500, and finally a hole, not visible here, on the opposite side of the base 492. Next, a release latch 528 having a latch tab 562 is inserted into a spring 546. This release latch 528 and spring 546 are placed into a recess, not shown here, in the bottom side of the clamp base 496. There is a corresponding slot 554 on lever 494 in which the release latch 528 can translate within when the spherical clamp 488 is assembled. The lever 494, in addition to the slot 554, also defines a channel 501, a tab 503, a hole 557 in the side of lever 494, and two holes 558 adjacent to the partial spherical clamp jaws 506. The lower partial spherical clamp jaws 506 further define a recess 560, which similar to the recess 508 on the upper partial spherical clamp jaws 504, are configured to allow some movement of a shaft connected to a spherical anchor, but also limit the pivotable travel and movement of a shaft connected to a spherical anchor by nature of the size and shape of the recesses 560, 508 in the assembled spherical clamp 488. The final assembly steps shown in FIG. 12 involve the insertion of a spring 552, the placement of lever 494 onto the assembly, aligning holes 558 on the lever 494 with corresponding holes 526 on the clamp base 496. The pins 510 are inserted into holes 558 on the lever 494 and holes 526 on the clamp base 496 to pivotably attach the upper partial spherical clamp jaws 504 to the lower partial spherical clamp jaws 506. A latch pin 556 is then inserted into hole 557 in a position to interfere with and contact the latch tab 562 portion of the release latch 528 which is held captive in the structure of the spherical clamp 488.

Figure 13:
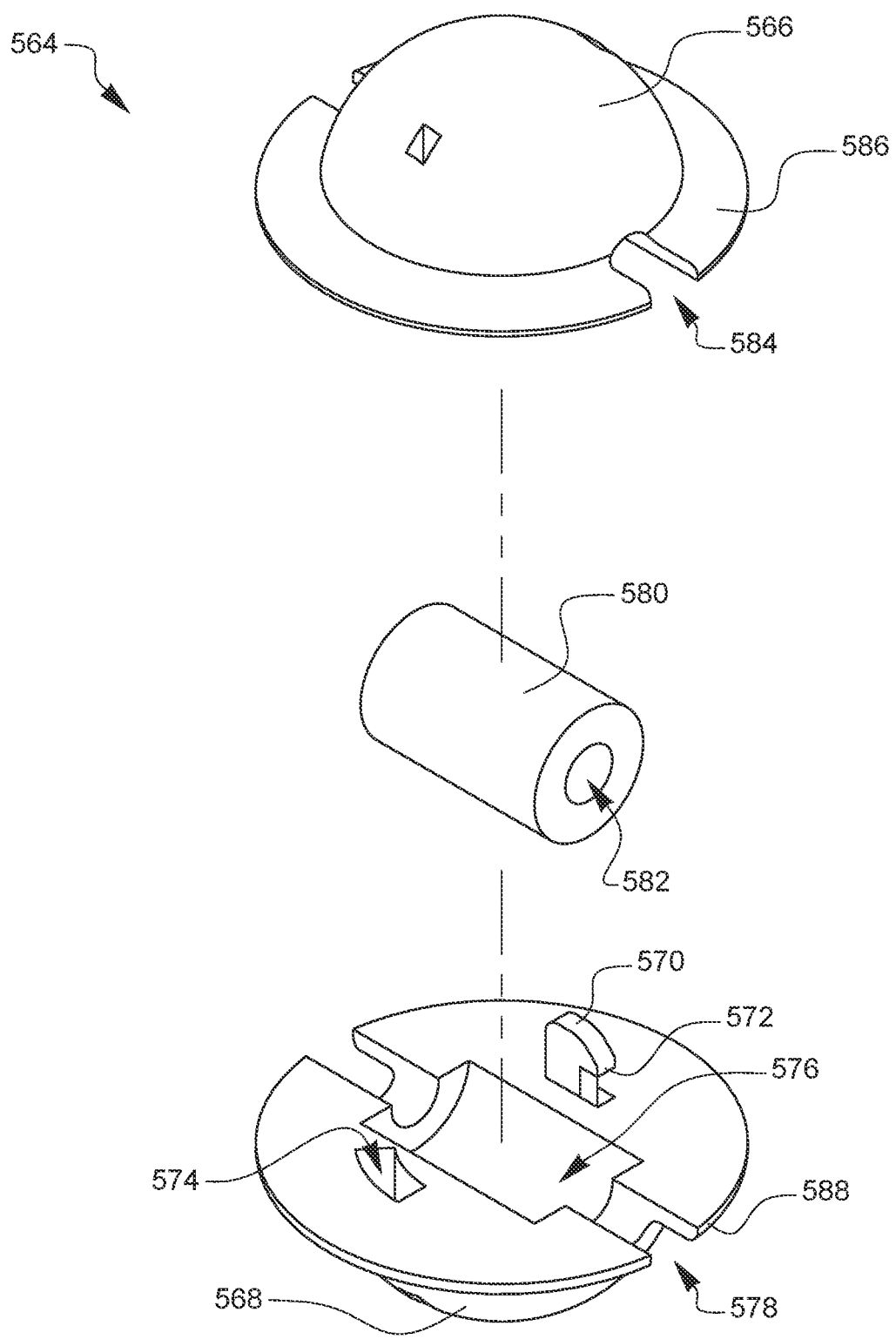
FIG. 13 is an exploded view of an embodiment of a spherical anchor used in minimally invasive surgical devices.

FIG. 13 is an exploded view of an embodiment of a spherical anchor system used in minimally invasive surgical devices. This embodiment of a spherical anchor 564 is constructed of a spherical anchor segment 566 having a circumferential protrusion 586 and a shaft recess portion 584 and a second spherical anchor segment 568 having a circumferential protrusion 588 and a shaft recess portion 578. The two spherical anchor segments 566, 568 are combined to form a singular spherical anchor 564 with a central compliant member 580 defining a shaft channel 582 held therebetween. The central compliant member 580 surrounds a shaft inserted through the spherical anchor 564 and provides a resilient, compliant, and compressive force directly onto the shaft to firmly and releasably hold the spherical anchor 564 and therefore the shaft of an instrument or device inserted therein. The combined shaft recess portions 584, 578 of the two spherical anchor segments 566, 568 are configured to allow a shaft or sleeve of an instrument to pass through a completed spherical anchor 564 when mated with a corresponding feature on another spherical anchor segment 568. While the shaft recess portion 584 illustrated in FIG. 13 has a shape and size that corresponds to a shaft or sleeve of the instruments shown and described herein, other embodiments of the spherical anchor 564 may have other shapes to accommodate other instrumentation or surgical devices. The spherical anchor segment 568 also defines a central recess 576 configured to hold a portion of the compliant member 580, a latch 570 having a tab 572, and a latch recess 574. Other embodiments may have a compliant member or recess that are not exactly centered within the spherical anchor and may be otherwise oriented. The latch recess 574 is configured to receive a corresponding latch and tab on the first spherical anchor segment 566 but not visible here. Similarly, the latch 570 and tab 572 on the second spherical anchor segment 568 are configured to be inserted into a corresponding latch recess, not shown here, on the internal surface of the first spherical anchor segment 566. The two spherical anchor segments 566, 568 are combined by inserting the compliant member 580 into the central recess 576 of the second spherical anchor segment 568, then placing the first spherical anchor segment 566 onto the second spherical anchor segment 568 while engaging the latch 570 and tab 572 into the corresponding recess on the first spherical anchor segment 566, and engaging the corresponding latch and tab on the first spherical anchor segment 566 into the latch recess 574 on the second spherical anchor segment 568. Once fixedly attached, there may be some intentional latitude in the tightness of the fit of the two spherical anchor segments 566, 568 for the purpose of allowing some compression on the two segments 566, 568 of the spherical anchor 564 by a spherical clamp such as the one described in regard to FIG. 11. While these spherical anchor segments 566, 568 are identical, interlocking, and configured to engage and connect concurrent with their identical structure, other embodiments may not have identical parts but still perform similarly configured functions as the ones described herein. When combined, the spherical anchor 564 structure also defines a circumferential protrusion 586, 588 that acts as a pivoting limiter when a conventional clamp is used, as opposed to the previously described spherical anchor clamp. While the partial spherical clamp jaws of the spherical anchor clamp limit the pivotable motion of the shaft or sleeve by virtue of the shaft or sleeve contacting the configured shape of the recess, a conventional clamp has no such features. The circumferential protrusion on the spherical clamp illustrated in FIG. 13 acts as the limiting feature by contacting the surfaces of a conventional clamp jaw while clamped onto a shaft or sleeve. This function limits the pivotability to a certain range which is appropriate for the procedural requirements of certain instrumentation and devices used in minimally invasive cardiac surgical procedures.

Figure 14A:
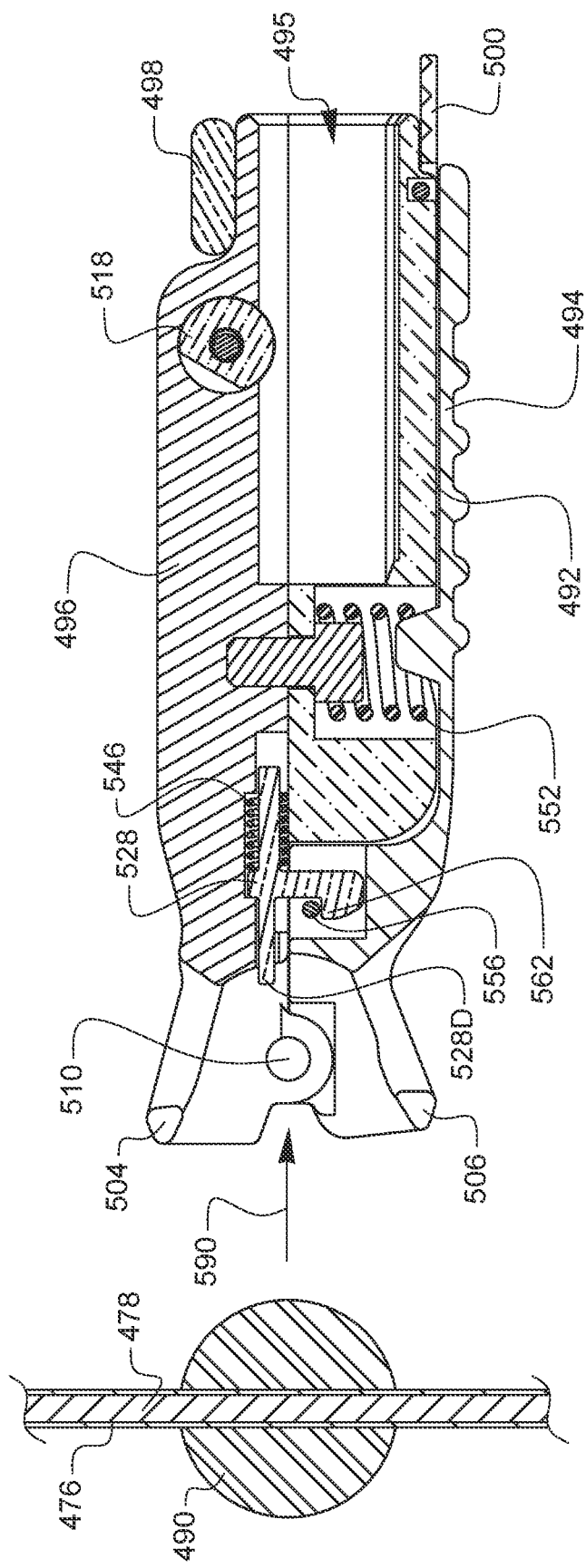
FIGS. 14A-14E are a series of cross-sectional side views illustrating the operation of the spherical anchor system of FIGS. 11-13.
Figure 14B:
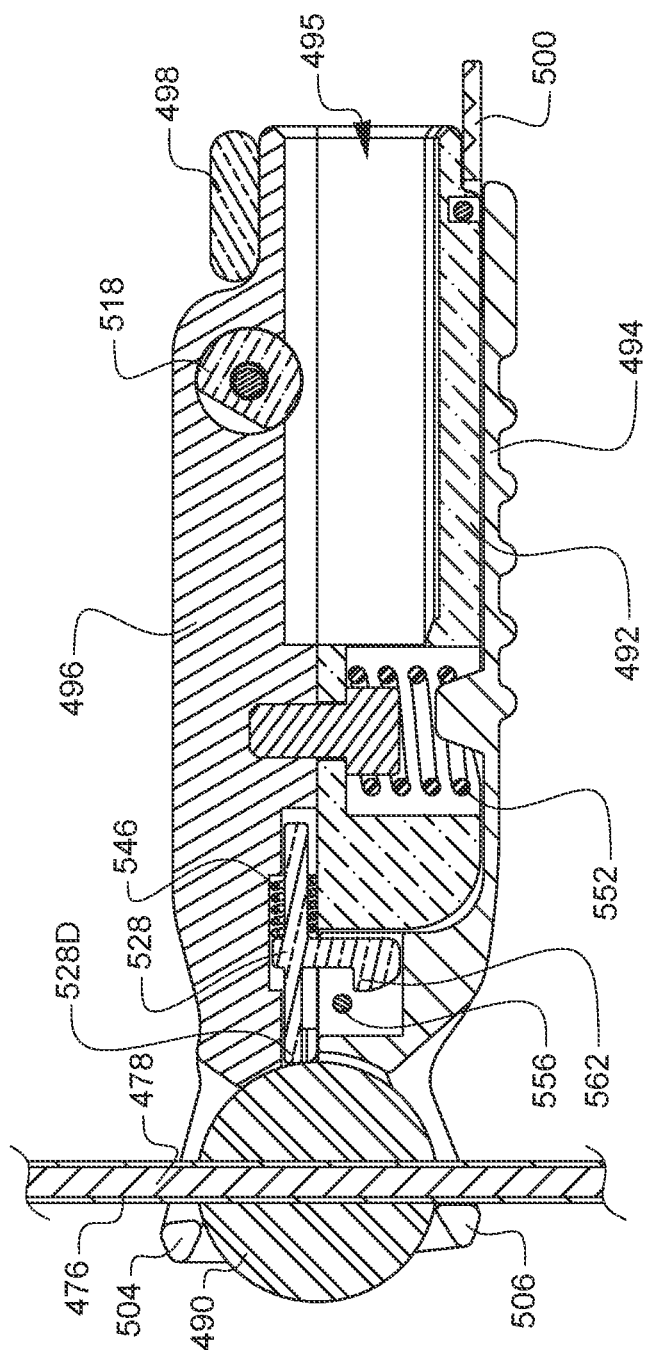

FIGS. 14A-14E are a series of cross-sectional side views illustrating the operation of the spherical anchor system of FIG. 11. FIG. 14A illustrates the spherical anchor system with the spherical anchor clamp 488 in an open position and the spherical anchor 490 having a sleeve 476 and the inner hinge rod 478 passing therethrough. The spherical anchor clamp 488 is also illustrated in cross-section, with the respective locations of the upper partial spherical clamp jaw 504, lower partial spherical clamp jaw 506, release latch 528, latch pin 556, clamp base 496, base 492, lever 494, compressed spring 552, and other features indicated. The positions of a distal end 528D of the release latch 528, the latch tab 562, and the spring 546 are also indicated. The spherical anchor 490 is engaged with and clamped into the spherical anchor clamp 488 by moving the spherical anchor 490 in direction 590. By moving the spherical anchor 490 in direction 590, the spherical anchor 490 contacts the distal end 528D of the release latch 528 and pushes the release latch 528 in direction 590 while compressing spring 546. When release latch 528 is moved in direction 590, the latch tab 562 is disengaged from the latch pin 556.

Figure 14C:
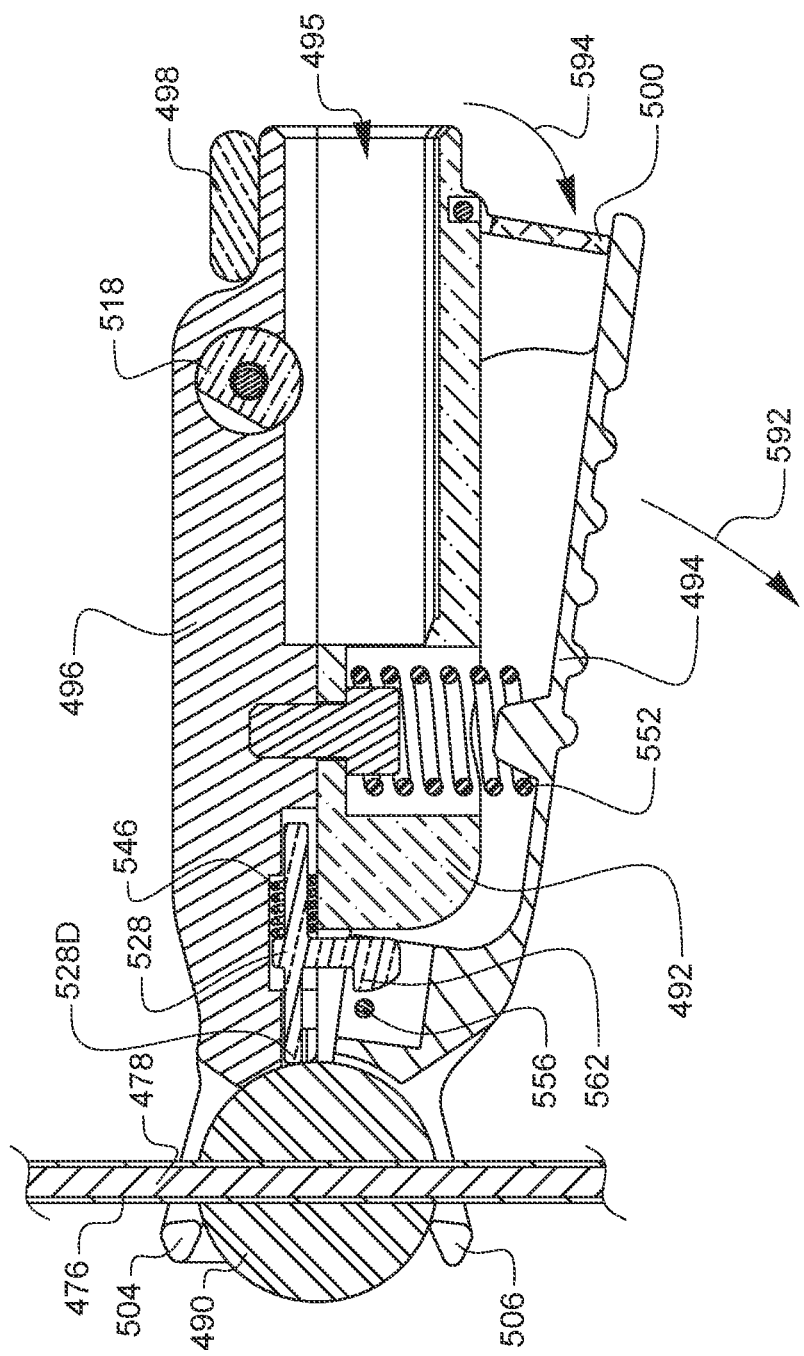
Figure 14D:
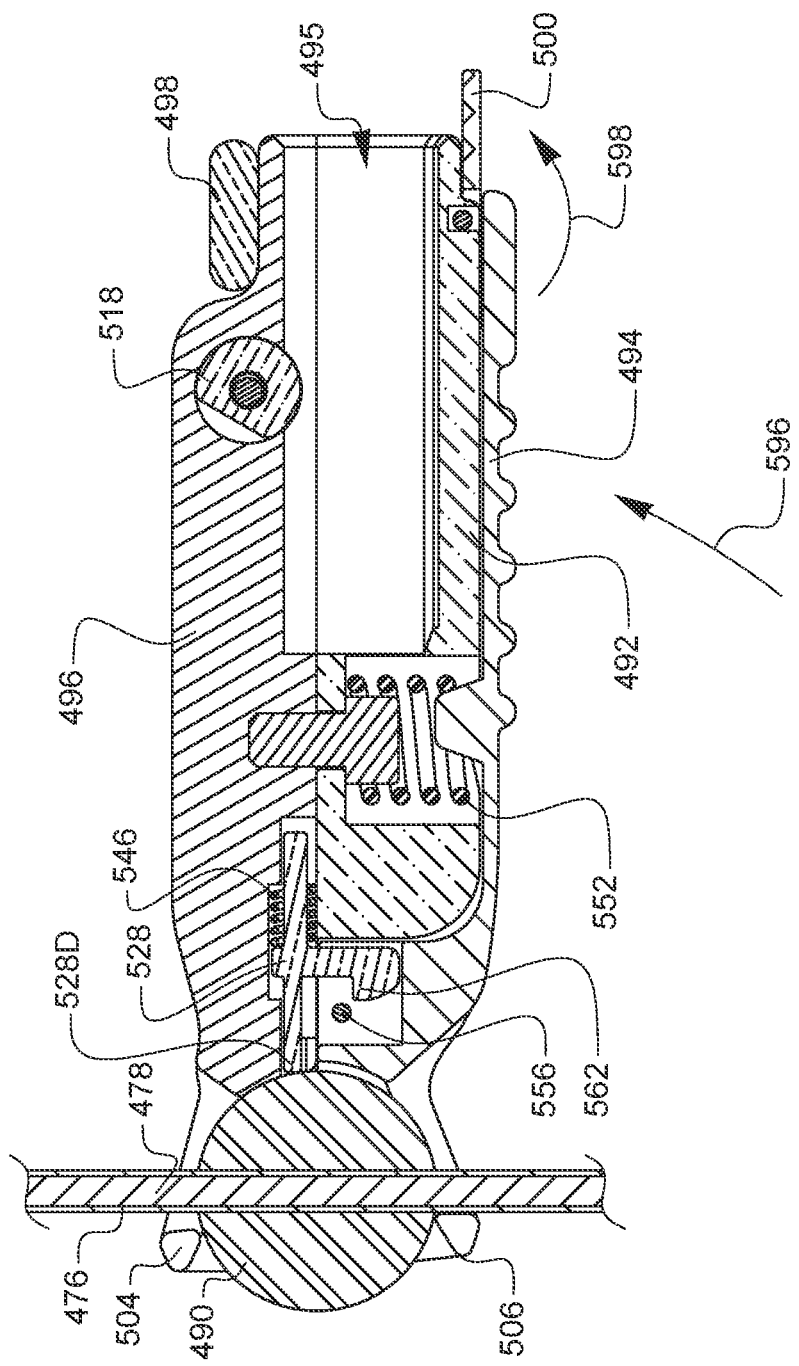
Figure 14E:
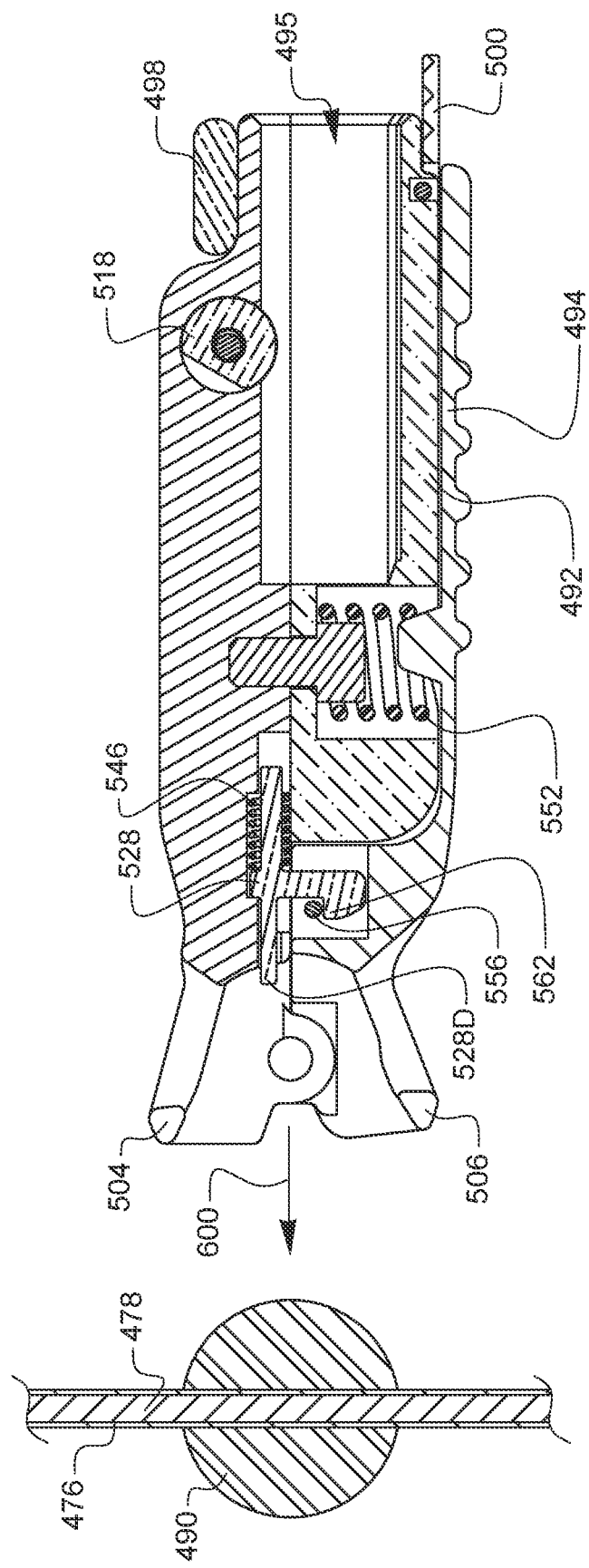

Once the spherical anchor 490 is in the desired position and pushed into the upper partial spherical clamp jaw 504 and lower partial spherical clamp jaw 506 of the spherical anchor clamp 488, and the latch tab 562 is released from the latch pin 556 as illustrated in FIG. 4B, the spherical anchor 490 is fully seated in and clamped into the inner space defined by upper partial spherical clamp jaw 504 and the lower partial spherical clamp jaw 506. FIG. 14C illustrates the release, in direction 592 of the lever 494 away from the clamp base 496 as spring 552 decompresses. Also shown in FIG. 14C is the movement of the interference latch 500, which was also held by a spring in a compressed state, moving in direction 594. The position of the interference latch 500, now braced between the base 492 and the lever 494 prevents the spherical anchor clamp 488 from being disengaged unintentionally. The steps described and shown in regard to FIGS. 14B and 14C may happen in sequence, nearly simultaneously, or simultaneously. The position of the upper partial spherical clamp jaw 504 and the lower partial spherical clamp jaw 506 illustrated in FIG. 14C surround the spherical anchor 490 such that it cannot be removed from the spherical anchor clamp 488 unless the spherical anchor clamp 488 is opened. One contributing factor to the clamping mechanism is that the partial spherical clamp jaw of the clamp base has a single arc center point and the partial spherical clamp jaw of the lever has a single arc center point as well. These respective single arcs are defined by the internal shape of walls of the upper and lower partial spherical clamp jaws 504, 506. These two partial spherical clamp jaws share substantially the same arc and the arcs share the same center point. In addition, the single arc center point of the combined clamp jaws 504, 506 is also coincident with the center point of the spherical anchor 490. The inner space and shape defined by the upper partial spherical clamp jaw 504 and the lower partial spherical clamp jaw 506 is also similar to the outer surface and shape of the spherical anchor 490 where in contact with the upper partial spherical clamp jaw 504 and the lower partial spherical clamp jaw 506. The rotation and pivoting of the spherical anchor 490 immobilized by being consistently clamped in the spherical anchor clamp 488 and the compliant squeezing of the spherical anchor 490 by the spherical anchor clamp 488 also immobilizes the movement of the sleeve 476 while held within the spherical anchor 490. FIG. 14D illustrates the release of the spherical anchor clamp 488 by moving interference latch 500 in direction 598 followed by squeezing the lever 494 towards the clamp base 496. This pivots the upper partial spherical clamp jaw 504 and the lower partial spherical clamp jaw 506 away from the spherical anchor 490, allowing it to be removed from the inner space defined by the upper partial spherical clamp jaw 504 and the lower partial spherical clamp jaw 506. Finally, FIG. 14E illustrates the spherical anchor 490 being removed from the spherical anchor clamp 488 by moving it in direction 600.

Figure 15:
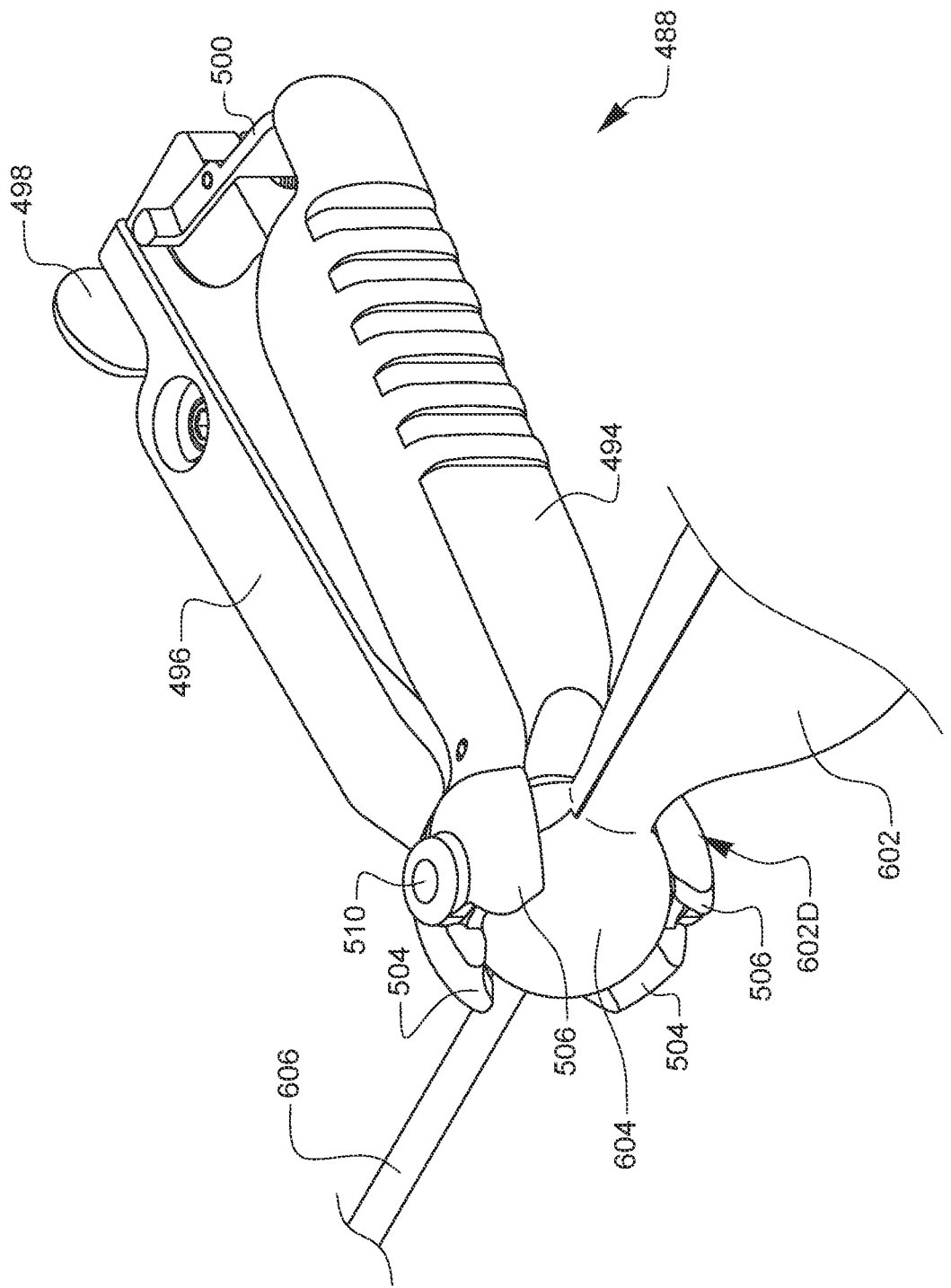
FIG. 15 is a top right front perspective view of a portion of a surgical instrument housing having a spherical anchor in combination with the spherical clamping system of FIG. 11.

FIG. 15 is a top right front perspective view of a portion of a surgical instrument housing having a spherical anchor in combination with the spherical clamping system of FIG. 11. FIG. 15 shows a surgical instrument having a housing 602 with a spherical anchor 604 incorporated into the distal end 602D of the housing 602 of the surgical instrument. While this embodiment shows the spherical anchor 604 incorporated into a housing 602 as a singular piece, other embodiments may have a spherical anchor attached by welding, screws, fasteners, or other means known to those skilled in the art. FIG. 15 illustrates the spherical anchor 604 of the instrument housing 602 engaged in the upper partial spherical clamp jaw 504 and the lower partial spherical clamp jaw 506 of the spherical anchor clamp 488.

The instruments and devices described herein may be used in various cardiac surgical procedures where suturing using a template or guide may facilitate the minimally invasive surgical procedure. One example of such a procedure is an anastomosis as part of minimally invasive IMA Harvesting and CABG procedure. Once the heart of a patient is accessed, the aorta is prepared, and a proximal anastomosis is completed, the surgical device including a suturing template may be introduced. Once the heart is positioned and visible through the window, the suturing template is placed through the 4th or 5th ICS incision.

Upon stabilization of the IMA graft with the use of the soft retainer and placement of the distal end (cobra head) on the U-channel zone of the AnastoPod™ or suturing template, the position of the AnastoPod™ is adjusted to allow minimum distance between the IMA cobra head and the targeted coronary artery site for creating the anasotomosis. Once the coronary arteriotomy is made, the suturing template is placed parallel to the arteriotomy site. To stabilize the IMA cobra head place the first stich at the toe (inside out) and then pass both ends of the suture through the suture deck or suturing template. When the desired tension is applied, the suture locking apparatus is engaged to maintain tension on the IMA graft.

The anastomosis is started at the toe (9 o'clock position) and worked towards the heel (3 o'clock position) by taking inside-out bites on the coronary artery and outside—in bites on the IMA graft. Once the back wall is completed, the suture lock apparatus mechanism is released, and the IMA graft is removed from the suturing template by lifting the soft retainer. The front wall is sutured in routine fashion and the anastomoses are completed using mechanical fasteners.

Various advantages of a minimally invasive surgical device used in cardiac surgery have been discussed above. Embodiments discussed herein have been described by way of example in this specification. It will be apparent to those skilled in the art that the foregoing detailed disclosure is intended to be presented by way of example only, and is not limiting. As just one example, although the end effectors in the discussed examples were often focused on the use of a scope, such systems could be used to position other types of surgical equipment. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A medical device assembly comprising:
   a hinge rod having a first portion and a second portion, the first portion extending along a rod axis from a first end to a second end, and the second portion extending along a support axis from a proximal end to a distal end, wherein the second end of the first portion is at or adjacent to the proximal end of the second portion;
   a pedestal coupled to a portion of the second portion of the hinge rod, the pedestal extending along a pedestal axis from a proximal end to a distal end, the pedestal comprising:
      a top surface;
      a first wall extending from the top surface;
      a second wall extending from the top surface, wherein an inner surface of the first wall and an inner surface of the second wall cooperate to define a trough that is configured to hold and guide a first portion of a vessel on a first portion of the top surface of the pedestal; and
      an articulation slot that extends from a perimeter edge of the pedestal, the articulation slot configured to receive a portion of the first portion of the hinge rod disposed at or adjacent to the second end of the first portion of the hinge rod, the articulation slot having a first indexed position comprising a first recess formed in a lateral edge partially defining the articulation slot and a second indexed position comprising a second recess formed in the lateral edge partially defining the articulation slot, wherein when the portion of the first portion of the hinge rod is disposed in the first indexed position, the pedestal tilts to a first tilt position relative to the second portion of the hinge rod, and when the portion of the first portion of the hinge rod is disposed in the second indexed position, the pedestal tilts to a second tilt position relative to the second portion of the hinge rod;
   a retainer movably coupled to a portion of the pedestal, the retainer having a planar member having a lower surface that is configured to oppose a second portion of the top surface of the pedestal, wherein the retainer is movably coupled to the portion of the pedestal such that the lower surface displaces along an axis normal to the pedestal axis from a first position in which the lower surface is a first distance from the second portion of the top surface of the pedestal to a second position in which the lower surface is a second distance from the second portion of the top surface of the pedestal, wherein in the second position, the lower surface is configured to contact a second portion of the vessel;
   a joint member coupled to the hinge rod; and
   a clamp assembly releasably coupled to the joint member such that when the clamp assembly is in a first locked configuration, the hinge rod is not repositionable with respect to the clamp assembly, and when the clamp assembly is in a second unlocked configuration, the hinge rod is repositionable with respect to the clamp assembly.

2. A medical device assembly of claim 1, further comprising a lever coupled to the hinge rod, wherein when the lever is in a first locked position, the hinge rod is not rotatable relative to the clamp assembly, and when the lever is in a second unlocked position, the hinge rod is rotatable about the rod axis relative to the clamp assembly.

3. A medical device assembly of claim 1, wherein the pedestal axis is parallel to the support axis.

4. A medical device assembly of claim 1, the pedestal comprising one or more surface elements formed on the second portion of the top surface of the pedestal.

5. A medical device assembly of claim 1, wherein the top surface of the pedestal extends along the pedestal axis and is normal to the rod axis.

6. A medical device assembly of claim 1, the pedestal further comprising a suturing template disposed at the distal end of the pedestal, the suturing template comprising one or more raised guiding features configured to engage and guide a portion of suture.

7. A medical device assembly of claim 1, wherein in the first position, the lower surface of the planar member of the retainer is in contact with or adjacent to the second portion of the top surface of the pedestal, and in the second position, the lower surface of the planar member of the retainer is remote from the second portion of the top surface of the pedestal.

8. A medical device assembly of claim 1, wherein the retainer is a soft retainer made of a resilient material.

9. A medical device assembly of claim 1, wherein the hinge rod is a hollow tube having an interior portion that is configured to receive a portion of suture.

10. A medical device assembly of claim 1, wherein the joint member is a spherical member that is coupled to the hinge rod.

11. A medical device assembly of claim 10, wherein the spherical member is coupled to a sleeve that is coupled to the hinge rod.

12. A medical device assembly of claim 11, wherein the spherical member comprises a first half component and a second half component, and the first half component and the second half component are configured to be displaceable along the sleeve.

13. A medical device assembly of claim 10, wherein the clamp assembly has a first jaw and a second jaw displaceable relative to the first jaw, and wherein a first surface of the first jaw is configured to contact a first portion of the spherical member when the clamp assembly is in the first locked configuration, and wherein a first surface of the second jaw is configured to contact a second portion of the spherical member when the clamp assembly is in the first locked configuration.

14. A medical device assembly of claim 13, wherein the first surface of the first jaw is concave and forms a complementary surface to the first portion of the spherical member and the first surface of the second jaw is concave and forms a complementary surface to the second portion of the spherical member.

15. A medical device assembly of claim 1, wherein each of the rod axis and the support axis is linear, and the rod axis is not parallel to the support axis.

16. A medical device assembly of claim 15, wherein the rod axis is offset from the support axis.

17. A medical device assembly of claim 16, wherein the rod axis is normal to the support axis.

18. A medical device assembly of claim 1, wherein the joint member is a spherical member that is coupled to a sleeve that is coupled to the hinge rod, and wherein the clamp assembly has a first jaw and a second jaw displaceable relative to the first jaw, and wherein a first surface of the first jaw is configured to contact a first portion of the spherical member when the clamp assembly is in the first locked configuration, and wherein a first surface of the second jaw is configured to contact a second portion of the spherical member when the clamp assembly is in the first locked configuration, and wherein the spherical member comprises a first half component and a second half component, when the clamp assembly is in the first locked configuration, the first half component and the second half component are not displaceable along the sleeve, and when the clamp assembly is in the second unlocked configuration, the first half component and the second half component are displaceable along the sleeve and rotatable relative to the clamp assembly.

\* \* \* \* \*